US009733257B2

(12) United States Patent
Cook et al.

(10) Patent No.: US 9,733,257 B2
(45) Date of Patent: Aug. 15, 2017

(54) BIOMARKERS OF OSTEOARTHRITIS

(71) Applicant: The Curators of the University of Missouri, Columbia, MO (US)

(72) Inventors: James L. Cook, Columbia, MO (US); Cristi R. Cook, Columbia, MO (US); Aaron M. Stoker, Columbia, MO (US); Keiichi Kuroki, Columbia, MO (US); Bridget Colleen Garner, Athens, GA (US); Richard Evans, Columbia, MO (US); Brandon Lee Roller, Naples, FL (US); Prakash Sidha Jayabalan, Columbia, MO (US)

( * ) Notice: Subject to any disclaimer, the term of this patent is extended or adjusted under 35 U.S.C. 154(b) by 0 days.

(21) Appl. No.: 15/290,613

(22) Filed: Oct. 11, 2016

(65) Prior Publication Data

US 2017/0030925 A1 Feb. 2, 2017

Related U.S. Application Data

(60) Division of application No. 14/175,254, filed on Feb. 7, 2014, now Pat. No. 9,488,646, and a continuation of application No. 13/041,055, filed on Mar. 4, 2011, now abandoned.

(51) Int. Cl.
*G01N 33/68* (2006.01)
*C12Q 1/68* (2006.01)
*G01N 33/53* (2006.01)

(52) U.S. Cl.
CPC ....... *G01N 33/6887* (2013.01); *C12Q 1/6883* (2013.01); *G01N 33/5308* (2013.01); *C12Q 2600/112* (2013.01); *C12Q 2600/136* (2013.01); *G01N 2333/52* (2013.01); *G01N 2333/5421* (2013.01); *G01N 2800/105* (2013.01); *G01N 2800/56* (2013.01)

(58) Field of Classification Search
CPC ................................ C12Q 1/68; C12Q 1/6883
See application file for complete search history.

(56) References Cited

U.S. PATENT DOCUMENTS 7,662,573 B2 2/2010 Ling et al.

OTHER PUBLICATIONS

Osteoarthritis Test; Lab Tests Online; American Association for Clinical Chemistry; https://labtestsonline.org/understanding/analytes/synovial/tab/test/; Sep. 10, 2013, pp. 1-3.*
Garner; The Identification of a Diagnostic Biomarker Panel for Canine Osteoarthritis; A Dissertation presented to the Faculty of the Graduate School at the University of Missouri-Columbia; pp. 1-154; published Jul. 2010.*

Altman, R. et al., Development of criteria for the classification and reporting of osteoarthritis. Classification of osteoarthritis of the knee. Diagnostic and Therapeutic Criteria Committee of the American Rheumatism Association, Arthritis Rheum., 1986, pp. 1039-1049, vol. 29, No. 8.
Andersson, M. et al., Serum Levels of Cartilage Oligomeric Matrix Protein (COMP) increase temporarily after physical exercise in patients with knee osteoarthritis, BMC Musculoskeletal Disorders, 2006, 8 pages, vol. 7.
Angst, F. et al., Responsiveness of the WOMAC osteoarthritis index as compared with the SF-36 in patients with osteoarthritis of the legs undergoing a comprehensive rehabilitation intervention, Ann. Rheum. Dis., 2001, pp. 834-840, vol. 60.
Bay-Jensen, A.C. et al., Biochemical markers of type II collagen breakdown and synthesis are positioned at specific sites in human osteoarthritic knee cartilage, Osteoarthritis Cartilage, 2008, pp. 615-623, vol. 16, No. 5.
Chan, W.P. et al., Osteoarthritis of the Knee: Comparison of Radiography, CT, and MR Imaging to Assess Extent and Severity, AJR, 1991, pp. 799-806, vol. 157.
Chua, S.D. Jr. et al., Effect of an exercise and dietary intervention on serum biomarkers in overweight and obese adults with osteoarthritis of the knee, Osteoarthritis Cartilage, 2008, pp. 1047-1053, vol. 16, No. 9.
Cook, J.L. et al., Bipolar and monopolar radiofrequency treatment of osteoarthritic knee articular cartilage: acute and temporal effects on cartilage compressive stiffness, permeability, cell synthesis, and extracellular matrix composition, J. Knee Surg., 2004, pp. 99-108, vol. 17, No. 2.
Stoker, A.M. and Cook, J.L., Abstract—Affect of Potential Food Additive IB3656 on Inflammatory and Degradative Markers Using an in vitro Co-Culture Model of Osteoarthritis, Osteoarthritis Research Society, 2011, 1 page.
Garner, B.C. et al., Abstract—Cartilage Derived Cytokine, Chemokine, and Matrix Metalloproteinase Concentrations in Naturally Occurring Osteoarthritis, Osteoarthritis Research Society, 2010, 1 page.
Roller, B.L. et al., Abstract—Characterization of Meniscal Pathology with Molecular and Proteomic Analyses, Osteoarthritis Research Society, 2010, 1 page.
Cook, J.L. et al., Kinetic study of the replacement of porcine small intestinal submucosa grafts and the regeneration of meniscal-like tissue in large avascular meniscal defects in dogs, Tissue Eng., 2001, pp. 321-334, vol. 7, No. 3.
Cook, J.L. et al., Induction of meniscal regeneration in dogs using a novel biomaterial, Am. J. Sports Med., 1999, pp. 658-665, vol. 27, No. 5.
Cook, J.L. et al., Biocompatibility of three-dimensional chondrocyte grafts in large tibial defects of rabbits, Am. J. Vet. Res., 2003, pp. 12-20, vol. 64, No. 1.
Dvorak, L.D. et al., Effects of carprofen and dexamethasone on canine chondrocytes in a three-dimensional culture model of osteoarthritis, Am. J. Vet. Res., 2002, pp. 1363-1369, vol. 63, No. 10.

(Continued)

*Primary Examiner* — Antonio Galisteo Gonzalez
(74) *Attorney, Agent, or Firm* — Polsinelli PC

(57) ABSTRACT

Biomarkers, biomarker panels and methods for diagnosing osteoarthritis (OA) and determining treatment are disclosed, using measurement of the expression level of certain polypeptides in a test sample from a subject, including MCP1, IL8, KC, MMP2, MMP3, Apolipoprotein A1, and Apolipoprotein E. Related methods for monitoring OA treatment efficacy, diagnostic reagents, and kits are also described.

12 Claims, 3 Drawing Sheets

(56) References Cited

OTHER PUBLICATIONS

Fettig, A.A. et al., Observer variability of tibial plateau slope measurement in 40 dogs with cranial cruciate ligament-deficient stifle joints, Vet. Surg., 2003, pp. 471-478, vol. 32, No. 5.
Fox, D.B. and Cook, J.L., Synovial fluid markers of osteoarthritis in dogs, J. Am. Vet. Med. Assoc., 2001, pp. 756-761, vol. 219, No. 6.
Garcia-Seco, E. et al., Measurement of articular cartilage stiffness of the femoropatellar, tarsocrural, and metatarsophalangeal joints in horses and comparison with biochemical data, Vet. Surg., 2005, pp. 571-578, vol. 34, No. 6.
Garnero, P. et al., Relationships between biochemical markers of bone and cartilage degradation with radiological progression in patients with knee osteoarthritis receiving risedronate: the Knee Osteoarthritis Structural Arthritis randomized clinical trial, Osteoarthritis Cartilage, 2008, pp. 660-666, vol. 16, No. 6.
Greenberg, D.D. et al., Biochemical effects of two different hyaluronic acid products in a co-culture model of osteoarthritis, Osteoarthritis Cartilage, 2006, pp. 814-822, vol. 14, No. 8.
Henrotin, Y. et al., Type II collagen markers in osteoarthritis: what do they indicate?, Curr. Opin. Rheumatol., 2007, pp. 444-450, vol. 19, No. 5.
Hou, Y. et al., Retrospective Analysis for Genetic Improvement of Hip Joints of Cohort Labrador Retrievers in the United States: 1970-2007, PLoS One, 2010, 9 pages, vol. 5, No. 2.
Kellgren, J.H. and Lawrence, J.S., Radiological Assessment of Osteo-Arthrosis, Ann. Rheum. Dis., 1957, pp. 494-502, vol. 16.
Kuroki, K. et al., Mechanisms of action and potential uses of hyaluronan in dogs with osteoarthritis, J. Am. Vet. Med. Assoc., 2002, pp. 944-50, vol. 221, No. 7.
Kuroki, K. et al., The effects of TIMP-1 and -2 on canine chondrocytes cultured in three-dimensional agarose culture system, Osteoarthritis Cartilage, 2003, pp. 625-635, vol. 11, No. 9.
Kuroki, K. et al., Characterizing osteochondrosis in the dog: potential roles for matrix metalloproteinases and mechanical load in pathogenesis and disease progression, Osteoarthritis Cartilage, 2005, pp. 225-234, vol. 13, No. 3.
Lawrence, R.C. et al., Estimates of the Prevalence of Arthritis and Other Rheumatic Conditions in the United States—Part II, Arthritis and Rheumatism, 2008, pp. 26-35, vol. 58, No. 1.
Mazieres, B. et al., Molecular markers of cartilage breakdown and synovitis at baseline as predictors of structural progression of hip osteoarthritis. The ECHODIAH Cohort, Ann. Rheum. Dis., 2006, pp. 354-359, vol. 65.
Mazzuca, S.A. et al., Urinary levels of type II collagen C-telopeptide crosslink are unrelated to joint space narrowing in patients with knee osteoarthritis, Ann. Rheum. Dis., 2006, pp. 1055-1059, vol. 65.
Nganvongpanit, K. et al., Prospective evaluation of serum biomarker levels and cartilage repair by autologous chondrocyte transplantation and subchondral drilling in a canine model, Arthritis Research and Therapy, 2009, 9 pages, vol. 11.
Poole, A.R., Biochemical/immunochemical biomarkers of osteoarthritis: utility for prediction of incident or progressive osteoarthritis, Rheum. Dis. Clin. North Am., 2003, pp. 803-18, vol. 29, No. 4.
Ray, A. et al., Induction of Matrix Metalloproteinase 1 Gene Expression Is Regulated by Inflammation-Responsive Transcription Factor SAF-1 in Osteoarthritis, Arthritis and Rheumatism, 2003, pp. 134-145, vol. 48, No. 1.
Garner, B.C. et al., Abstract—Analysis of Cartilage Derived Proteins as Potential Biomarkers for Early OA, Osteoarthritis Research Society, 2010, 1 page.
Stoker, A.M. et al., Site-specific analysis of gene expression in early osteoarthritis using the Pond-Nuki model in dogs, Journal of Orthopaedic Surgery and Research, 2006, 12 pages, vol. 1, No. 8.
Van Spil, W.E. et al., Serum and urinary biochemical markers for knee and hip-osteoarthritis: a systematic review applying the consensus BIPED criteria, Osteoarthritis Cartilage, 2010, pp. 605-612, vol. 18, No. 5.

Ware, Jr, J.E. and Sherbourne, C.D., The MOS 36-item Short-Form Health Survey (SF-36): III. Tests of data quality, scaling assumptions, and reliability across diverse patient groups, Med. Care, 1994, pp. 40-66, vol. 32, No. 1.
Wilke, V.L. et al., Estimate of the annual economic impact of treatment of cranial cruciate ligament injury in dogs in the United States, J. Am. Vet. Med. Assoc., 2005, pp. 1604-1607, vol. 227, No. 10.
Yoshimura, M. et al., Evaluation of the effect of glucosamine administration on biomarkers for cartilage and bone metabolism in soccer players, Int. J. Mol. Med., 2009, pp. 487-94, vol. 24, No. 4.
Garner, B.C. et al., Abstract—Synovial Fluid and Serum Derived Chemokine and Matrix Metalloproteinase Concentrations and Alterations in Proteins in Spontaneous Osteoarthritis, Osteoarthritis Research Society, 2011, 1 page.
Roller, B.L. et al., Abstract—Identification of Novel Synovial Fluid Biomarkers that Correlate with Meniscal Pathology, Osteoarthritis Research Society, 2010, 1 page.
Roller, B.L. et al., Abstract—Analysis of Synovial Fluid Biomarkers and Correlation with Radiography, Osteoarthritis Research Society, 2010, 1 page.
Garner, B.C. et al., Abstract—Synovial Fluid Derived Chemokine Concentrations in Induced Osteoarthritis, Osteoarthritis Research Society, 2010, 1 page.
European Search report regarding Application No. 11751442.2, issued Jul. 18, 2013, 11 pages.
Lisignoli, Gina Et al., Different Chemokines are Expressed in Human Arthritic Bone Biopsies: IFN-y and IL-6 Differently Modulate IL-8, MCP-1 and Rantes Production by Arthritic Osteoblasts, Cytokine, 2002, pp. 231-238, vol. 20, No. 5.
Garner, B.C. et al, Abstract Only, Using animal models in osteoarthritis biomarker research, J. Knee Surg., 2011, pp. 251-64, vol. 24, No. 4.
Garnero, P., Use of biochemical markers to study and follow patients with osteoarthritis, Current Rheumatology Reports, 2006, pp. 37-44, vol. 8.
Juarranz, M.G. et al, Vasoactive intestinal peptide modulates proinflammatory mediator synthesis in osteoarthritic and rheumatoid synovial cells, Rheumatology, 2004, pp. 416-422, vol. 43.
Degner; "Arthrocentesis in Dogs"; Clinician's Brief; Aug. 2014; pgs. 69-74.
Balakrishnan et al.; "Differential proteomic analysis of synovial fluid from rheumatoid arthritis and osteoarthritis patients"; Clinical Proteomics 2014; 11:1; pp. 1-1'4.
Kraus; "Oars! World Congress—Brussels 2010 Year in Review—Biochemical Markers"; Osteoarthritis Cartilage Apr. 2011; 19(4); pp. 346-353.
Pettitt; Investigation and management of canine osteoarthritis'; Canine Mobility; http://inpractice.bmj.com/on Dec. 14, 2015; (9 pages).
Pettitt; Investigation and management of canine osteoarthritis; Canine Mobility; http://inpractice.bmj.com/on Dec. 14, 2015; (9 pages).
Mobasheri; "Osteoarthritis year 2012 in review: biomarkers"; Osteoarthritis and Cartilage 20 (2012); pp. 14511464.
Howell et al.; "Diagnostic Cytology and Hematology of the Dog and Cat"; Third Edition Mosby Elsevier; Chapter 12; 2008; (5 pages).
Affymetrix: "GeneChip Canine Genome 2.0 Array" Announcement Affymetrix, (Jan. 1, 2005), XP002480398.
International Search Report regarding PCT/US2011/27242 dated Jul. 27, 2011, 12 pages.
Australian Patent Examination Report regarding Application No. 2011222558 dated Apr. 30, 2014, 5 pages.
Hegemann, N. et al, Biomarkers of joint tissue metabolism in canine osteoarthritic and arthritic joint disorders, Osteoarthritis Cartilage, 2002, Abstract, vol. 10, No. 9.
Bondeson, J. et al., "The Role of Synovial Macrophages and Macrophage-produced . . . "; Arthritis Research & Therapy, 2006, pp. 1-12, vol. 8, No. R187.
Lotz, M. et al, Cartilage and Joint Inflammation, J. of Immunology, 1992, pp. 466-473, vol. 148, No. 2.

(56) References Cited

OTHER PUBLICATIONS

Blackburn, W.D. et al, Cartilage Imaging in Osteoarthritis, Seminars in Arthritis and Theumatism, 1996, pp. 273-281, vol. 25, No. 4.
Cook, J.L. et al, Evaluation of Small Intestinal Submucosa Grafts for Meniscal Regeneration in a Clinically Relevant Posterior Meniscectomy Model in Dogs, J. Knee Surgery, 200.
Garner, B.C. et al, Abstract Changes in Cytokine and Chemokine Levels in teh Synovial Fluid, Serum and Urine of Dogs with Surgically Induced Osteoarthritis, Osteoarthritis Res.
Roy, R.G. et al, A Retrospective Evaluation of Stifle Osteoarthritis in Dogs with Bilateral Medial Patellar Luxation and Unilateral Surgical Repair, Veterinary Surgery, 1992.
Bellamy, N. et al, Validation Study of WOMAC: A Health Status Instrument for Measuring CLincially Important Patient Relevant Outcomes to Antirheumatic Drug Therapy in Patients.
Office Action dated Sep. 2, 2014 by JP Patent Office; JP Patent Application No. 2012-556266; filed Mar. 4, 2011; Applicant—University of Missouri (Columbia).
Office Action dated Oct. 20, 2015 by JP Patent Office; JP Patent Application No. 2014-244355; filed Mar. 4, 2011; Applicant—University of Missouri (Columbia).

* cited by examiner ic text content of page 1 and 2 below:

BIOMARKERS OF OSTEOARTHRITIS

REFERENCE TO RELATED APPLICATIONS

This application is a divisional of U.S. application Ser. No. 14/175,254, filed Feb. 7, 2014, which is a continuation of U.S. patent application Ser. No. 13/041,055, filed Mar. 4, 2011, which claims the benefit of U.S. Patent Application No. 61/339,511, filed Mar. 5, 2010, the entire contents all of which are herein incorporated by reference.

FIELD OF THE INVENTION

The present disclosure relates to biomarkers of disease and more particularly to a plurality of biomarkers, related methods and kits for diagnosing, staging, and monitoring 10 osteoarthritis.

BACKGROUND

Osteoarthritis (OA) is a debilitating disease that affects human and veterinary, particularly canine patients. Because OA is not typically diagnosed early enough to prevent the clinical progression of disease, development of early OA biomarkers has profound ramifications for diagnostic screening, disease staging, treatment planning and monitoring. In dogs, certain proteins exhibit differential expression levels in synovial fluid when OA is experimentally induced. These are monocyte chemoattractant protein 1 (MCP1), interleukin 8 (IL8) and keratinocyte derived chemoattractant (KC), certain Apolipoproteins, and matrix metalloproteinases (MMPs). It is unknown however whether these or other proteins might be useful as potential biomarkers in spontaneously occurring OA in dogs or in other species including humans. Given the high potential value in being able to apply proteomics methods to diagnosis and prognosis of OA disease, and treatment monitoring and elucidation of OA disease mechanisms, it would be useful to identify new OA biomarkers and biomarker combinations with the ability to conveniently and reliably discriminate between individuals in which OA is present and those in which OA is not present, and determine the type and severity of disease burden.

SUMMARY OF THE INVENTION

In one aspect, the present disclosure provides a method for diagnosing, staging, or monitoring osteoarthritis in a subject comprising: measuring in a biological sample from the subject the level of expression of at least two polypeptides selected from the group consisting of: MCP1, IL8, KC, MMP2, MMP3, MMP9, IL6, MMP1, RANTES, IL1B, Apolipoprotein A1, Apolipoprotein E, DCN, CILP and COMP, and fragments of any thereof, and any combination thereof, wherein the expression levels of the at least two polypeptides or fragments thereof in the biological sample provide a sample protein expression profile indicative of the presence or absence, degree, severity, type or stage of osteoarthritis in the subject. The method may further comprise comparing the sample protein expression profile to a control protein expression profile, wherein a difference between the sample protein expression profile and the control protein expression profile is indicative of the presence or absence, degree, severity, type or stage of osteoarthritis in the subject. In the method, the subject can be at risk of having or is suspected of having osteoarthritis. The level of expression of the at least two polypeptides in the biological sample can be measured by many methods as detailed further herein below, including but not limited to detecting alterations in DNA due to a process selected from the group consisting of DNA amplification, DNA methylation/demethylation, and single nucleotide polymorphisms. In another aspect, the present disclosure provides an OA biomarker expression profile comprising polypeptide expression level information for two or more polypeptides selected from the group consisting of: MCP1, IL8, KC, MMP2, MMP3, IL6, MMP1, RANTES, MMP9, IL1B, Apolipoprotein A1, Apolipoprotein E, DCN, CILP and COMP and fragments of any thereof, and any combination thereof, obtained from a biological sample from a subject suspected of having osteoarthritis. An OA expression profile may further comprise polypeptide expression level information for at least one biological sample obtained from at least one healthy subject. Biological samples from the subject suspected of having osteoarthritis and the healthy subject or subjects may each comprise a sample of synovial fluid, a sample of whole blood, a sample of blood plasma, a sample of serum, a sample of urine, or a sample of saliva. Preferably, the biological samples are samples of synovial fluid. Multiple biological samples of the same or different type may be obtained from each subject, OA expression level information obtained from each sample, and the results combined in a single OA expression profile. In another aspect, the present disclosure provides a diagnostic reagent for osteoarthritis comprising two or more antibodies against any two or more OA biomarkers or fragments thereof selected from the group consisting of: MCP1, IL8, KC, MMP2, MMP3, IL6, MMP1, RANTES, MMP9, IL1B, Apolipoprotein A1, Apolipoprotein E, DCN, CILP and COMP and fragments of any thereof. The diagnostic reagent may be provided in a kit. In another aspect, the present disclosure provides a kit for diagnosing osteoarthritis in a subject, the kit comprising: at least two OA biomarker detection reagents that each specifically bind to an OA polypeptide selected from the group consisting of MCP1, IL8, KC, MMP2, MMP3, IL6, MMP1, RANTES, MMP9, IL1B, Apolipoprotein A1, Apolipoprotein E, DCN, CILP and COMP and fragments of any thereof, or at least two OA biomarker detection reagents that each specifically bind to at least part of a polynucleotide sequence coding for at least two of the OA polypeptides, wherein the specific binding of the reagent is indicative of the expression level of at least one OA polypeptide in a biological sample from a subject. In the kit, the at least one reagent that specifically detects expression of at least one biomarker may comprise a nucleic acid probe complementary to at least part of a polynucleotide sequence coding for one of the polypeptides. A nucleic acid probe can be a cDNA or an oligonucleotide. The at least one OA biomarker detection reagent can be immobilized on a substrate surface. The kit may comprise at least two biomarker detection reagents arranged on the substrate surface.

In the kit, at least two biomarker reagents can be arranged on a substrate surface to comprise a microarray. In another aspect, the present disclosure provides a method for identifying a candidate substance as a therapeutic agent for treating osteoarthritis, comprising: a) administering the candidate substance to a subject diagnosed with spontaneous osteoarthritis; b) measuring the expression level of two or more OA polypeptides selected from the group consisting of MCP1, IL8, KC, MMP2, MMP3, IL6, MMP1, RANTES, MMP9, IL1B, Apolipoprotein A1, Apolipoprotein E, DCN, CILP and COMP in a biological sample from the subject; and c) selecting the candidate substance as a candidate therapeutic agent for treating osteoarthritis if the expression level of each of the two or more OA polypeptides in the biological sample is lower than or equal to the expression level for the selected two or more OA polypeptides in a biological sample from a control subject not administered the test substance.

In another aspect, the present disclosure provides a method for monitoring the effect of a treatment of osteoarthritis in a subject comprising: a) obtaining a first OA biomarker expression profile comprising measuring the expression level of two or more OA polypeptides selected from the group consisting of MCP1, IL8, KC, MMP2, MMP3, IL6, MMP1, RANTES, MMP9, IL1B, Apolipoprotein A1, Apolipoprotein E, DCN, CILP and COMP in a first biological sample obtained from the subject before the osteoarthritis treatment is administered to the subject; b) obtaining a second OA biomarker expression profile comprising measuring the expression level of the two or more OA polypeptides selected in (a), in a second biological sample obtained from the subject after or while the osteoarthritis treatment is administered to the subject; and c) comparing the first OA biomarker expression profile with the second OA biomarker expression profile, wherein if the expression level of each of the two or more selected OA polypeptides in the first OA biomarker expression profile is lower than or equal to the expression level for the selected two or more OA polypeptides in the second biological sample from the subject is indicative of a therapeutic effect of the osteoarthritis treatment in the subject.

In another aspect, the present disclosure provides a method for treating osteoarthritis in a canine subject comprising: (i) requesting the results of a first biomarker profile analysis of a test biological fluid sample from the subject and (ii) administering a treatment for OA to the subject when the results of the biomarker profile analysis are indicative of the presence of OA in the subject, wherein the biomarker profile analysis comprises: (a) measuring an expression level of at least two osteoarthritis marker polypeptides in the test sample using a protein detection method to determine a first OA biomarker profile, wherein the osteoarthritis marker polypeptides are selected from the group consisting of: MCP1, IL8, and KC; (b) measuring an expression level of each osteoarthritis marker polypeptide used in (a) in a control biological fluid sample from a control canine subject in which OA is not present using the protein detection method used in (a) to determine a second OA biomarker profile; and (c) comparing the first OA biomarker profile from (a) to the second OA biomarker profile from (b) wherein a difference between the first OA biomarker profile and the second OA biomarker profile is indicative of the presence of osteoarthritis in the subject. In the method, the level of expression of all three of MCP1, IL8, and KC can be measured. The level of expression of at least one additional osteoarthritis marker polypeptide can be measured. The at least one additional osteoarthritis marker polypeptide can be selected for example from the group consisting of MMP2 and MMP3. The method may include for example measuring in the biological fluid samples from the canine test and control subjects the level of expression of all five of MCP1, IL8, KC, MMP2 and MMP3. The method may further comprise measuring in the biological fluid samples from the canine test and control subjects the level of expression of at least one additional osteoarthritis marker selected from Apolipoprotein A1 and Apolipoprotein E. The method may include measuring the level of expression of at least seven osteoarthritis marker polypeptides. The method may further include monitoring the effect of the treatment of osteoarthritis in the subject by obtaining the results of a second biomarker profile analysis and comprising the results to the first biomarker profile analysis. In such a method, the selected osteoarthritis marker polypeptides may comprise MCP-1, IL8, KC, MMP2, MMP3, Apolipoprotein A1 and Apolipoprotein E. The subject may be at risk of having, or is suspected of having osteoarthritis. The protein detection method used may be selected from the group consisting of: LUMINEX, ELISA, immunoassay, mass spectrometry, high performance liquid chromatography, two-dimensional electrophoresis, Western blotting, protein microarray, and antibody microarray. In an exemplary method, the protein detection method is an immunoassay.

In any of the above methods, the biological sample or samples may comprise any one of synovial fluid, whole blood, blood plasma, serum, urine, and saliva. In an exemplary method, the biological sample(s) comprise synovial fluid. Preferably, the level of expression of at least four polypeptides is measured. In any of the methods, the subject may be a mammal. Preferably the subject is a human or a canine. In an exemplary embodiment of any of the above methods, the subject is a canine and the method may comprise measuring in a biological sample from the subject the level of expression of MCP1, IL8, KC, MMP2 and MMP3, or fragments thereof. In another exemplary embodiment of any of the above methods, the subject is a human and the method may comprise measuring in a biological sample from the subject the level of expression of MCP1, IL6, IL8, KC and MMP1, or fragments thereof. Such a method may further comprise measuring in the biological sample the level of expression of RANTES, or fragments thereof. In any of the above methods, the expression level of each of the at least two polypeptides in the biological sample from the subject is measured using a method selected from the group consisting of: LUMINEX, ELISA, immunoassay, mass spectrometry, high performance liquid chromatography, two-dimensional electrophoresis, qPCR, RT-PCR, nucleic acid microarray, in situ hybridization, SAGE, Western blotting, protein microarray, and antibody microarray.

DETAILED DESCRIPTION OF THE INVENTION

A. Definitions

Figure 1A:
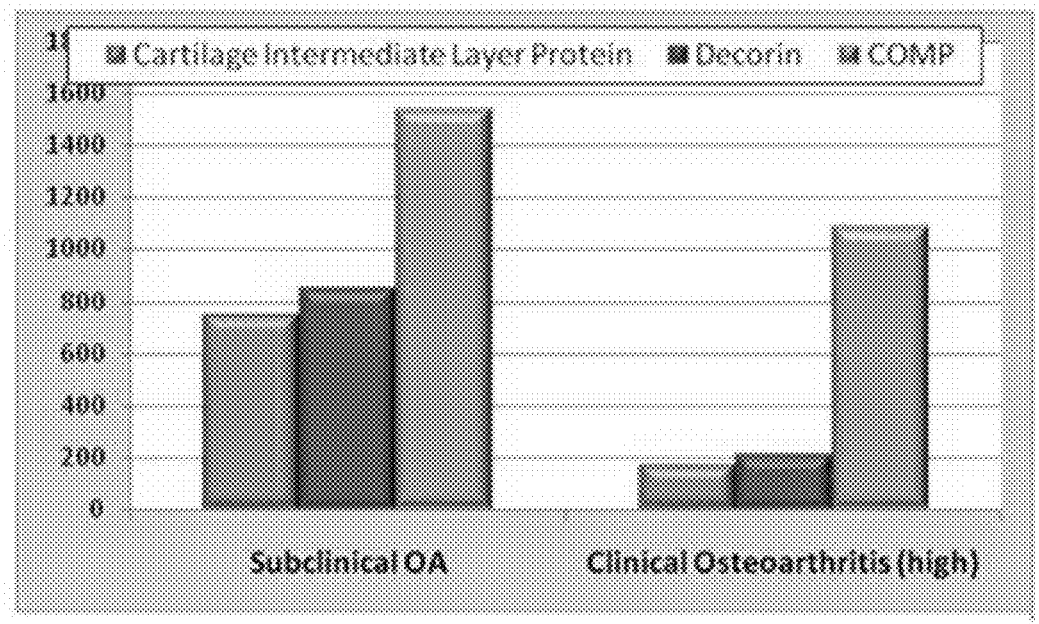
FIG. 1A is a bar graph showing levels (Mean±SE concentrations (pg/ml)), of Cartilage Intermediate Layer Protein (CILP), Decorin and COMP in dogs with subclinical OA and in dogs with clinical OA following removal of high abundance proteins.

Section headings as used in this section and the entire disclosure herein are not intended to be limiting.

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

a) Antibody

As used herein, the term "antibody" refers to a protein consisting of one or more polypeptides substantially encoded by immunoglobulin genes or fragments of immunoglobulin genes, and encompasses polyclonal antibodies, monoclonal antibodies, and fragments thereof, as well as molecules engineered from immunoglobulin gene sequences. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

b) Detectable Label

As used herein the term "detectable label" refers to any moiety that generates a measurable signal via optical, electrical, or other physical indication of a change of state of a molecule or molecules coupled to the moiety. Such physical indicators encompass spectroscopic, photochemical, biochemical, immunochemical, electromagnetic, radiochemical, and chemical means, such as but not limited to fluorescence, chemifluorescence, chemiluminescence, and the like.

c) Marker

The terms "marker" or "biomarker" as used interchangeably herein refer to any molecule used as a target for analyzing test samples obtained from subjects, and encompass proteins or polypeptides themselves as well as antibodies against same that may be present in a test sample. Proteins or polypeptides used as a marker include any variants and fragments thereof, and in particular, immunologically detectable fragments. For example, it is appreciated that variants of a marker polypeptide are encoded by the same gene, but can differ in their isoelectric point or molecular weight or both as a result of alternative processing such as alternative splicing and/or differences in post-translational modification (e.g., glycosylation, acylation, and/or phosphorylation). It will further be appreciated that cellular proteins can be damaged as a result of a disease process such as inflammation and may fragment and thus that proteins or polypeptides used as a marker according to the present disclosure include fragments thereof. Additionally it will be recognized that certain markers can be synthesized in an inactive form that is subsequently converted to an active form by proteolysis. Proteins or fragments thereof can also occur as part of a complex. Proteins or polypeptides used as markers according to the present disclosure also include such complexes. The terms "biomarker" and "marker" also encompass nucleic acid molecules comprising a nucleotide sequence that codes for a marker protein, and also polynucleotides that can hybridize under stringent conditions with a part of such nucleic acid molecules. An "OA biomarker" and "OA marker" as used interchangeably herein, refer to a protein, polypeptide, antibodies against same and any fragment thereof, that may be present in a test sample from a subject, and has an expression level that has been found to be indicative of the presence of OA in the subject as described herein, and these terms also encompass any nucleic acid molecule comprising a nucleotide sequence that codes for an OA marker protein.

d) Subject

As used herein, the terms "subject" and "patient" are used interchangeably irrespective of whether the subject has or is currently undergoing any form of treatment. As used herein, the terms "subject" and "subjects" refer to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous monkey, chimpanzee, etc) and a human). Preferably, the subject is a canine or a human.

e) Test Sample

As used herein, the term "test sample" generally refers to a biological material being tested for and/or suspected of containing an analyte of interest. The biological material may be derived from any biological source but preferably is a biological fluid likely to contain the analyte of interest. Examples of biological materials include, but are not limited to, stool, whole blood, serum, plasma, red blood cells, platelets, interstitial fluid, saliva, ocular lens fluid, cerebral spinal fluid, sweat, urine, ascites fluid, mucous, nasal fluid, sputum, synovial fluid, peritoneal fluid, vaginal fluid, menses, amniotic fluid, semen, soil, etc. Preferably, the test sample is a synovial fluid sample.

The test sample may be used directly as obtained from the biological source or following a pretreatment to modify the character of the sample. For example, such pretreatment may include preparing plasma from blood, diluting viscous fluids and so forth. Methods of pretreatment may also involve filtration, precipitation, dilution, distillation, mixing, concentration, inactivation of interfering components, the addition of reagents, lysing, etc. If such methods of pretreatment are employed with respect to the test sample, such pretreatment methods are such that the analyte of interest remains in the test sample at a concentration proportional to that in an untreated test sample (e.g., namely, a test sample that is not subjected to any such pretreatment method(s)).

f) Osteoarthritis

As used herein, the term "osteoarthritis" (abbreviated as "OA"), refers to the disease also known as osteoarthrosis and degenerative joint disease, characterized by inflammation and damage to, or loss of cartilage in any joint or joints, and joint pain. Clinical standards for diagnosing osteoarthritis in subjects including mammalian subjects such as canines and humans are well known and include for example swelling or enlargement of joints, joint tenderness or pain, decreased range of motion in joints, visible joint deformities such as bony growths, and crepitus. Symptoms can be identified by clinical observation and history, or imaging including MRI and X-ray. Criteria for diagnosing the presence or absence of OA and severity or degree of OA include but are not limited to the ACR Criteria for knee OA (R. Altman et al., Development of criteria for the classification and reporting of osteoarthritis: Classification of osteoarthritis of the knee: Diagnostic and Therapeutic Criteria Committee of the American Rheumatism Association. ARTHRITIS RHEUM. August 29(8):1039-1049(1986)), functional status criteria according to WOMAC (N. Bellamy et al., 1988, Validation study of WOMAC: a health status instrument for measuring clinically important patient relevant outcomes to antirheumatic drug therapy in patients with osteoarthritis of the hip or knee. J RHEUMATOL 15:1833-1840), and radiological standards for evaluating OA disease severity according to the Kellgren and Lawrence method for knee OA (Kellgren, J. H. and J. S. Lawrence, Radiological assessment of osteo-arthrosis. ANN RHEUM DIS 16:494-502).

g) Expression

The term "expression," as used herein, refers to the conversion of the DNA sequence information into messenger RNA (mRNA) or protein. Expression may be monitored by measuring the levels of full-length mRNA, mRNA fragments, full-length protein, or protein fragments. Expression may also be inferred by assessing alterations in the DNA relative to a control state. Alterations in DNA that affect expression include amplification (increased copy number) of the DNA, changes in the methlyation status of the regulatory region of a gene, or single nucleotide polymorphisms in the regulatory region of a gene.

h) Hybridization

The term "hybridization," as used herein, refers to the process of annealing or base-pairing via specific hydrogen bonds between two complementary single-stranded nucleic acids. The "stringency of hybridization" is determined by the conditions of temperature and ionic strength. Nucleic acid hybrid stability is expressed as the melting temperature or Tm, which is the temperature at which the hybrid is 50% denatured under defined conditions. Equations have been derived to estimate the Tm of a given hybrid; the equations take into account the G+C content of the nucleic acid, the length of the hybridization probe, etc. (e.g., Sambrook et al, 1989, chapter 9). To maximize the rate of annealing of the probe with its target, hybridizations are generally carried out in solutions of high ionic strength (6×SSC or 6×SSPE) at a temperature that is about 20-25° C. below the Tm. If the sequences to be hybridized are not identical, then the hybridization temperature is reduced 1-1.5° C. for every 1% of mismatch. In general, the washing conditions are as stringent as possible (i.e., low ionic strength at a temperature about 12-20° C. below the calculated Tm). As an example, highly stringent conditions typically involve hybridizing at 68° C. in 6×SSC/5×Denhardt's solution/1.0% SDS and washing in 0.2×SSC/0.1% SDS at 65° C. The optimal hybridization conditions generally differ between hybridizations performed in solution and hybridizations using immobilized nucleic acids. One skilled in the art will appreciate which parameters to manipulate to optimize hybridization.

i) Nucleic Acid Molecule

The term "nucleic acid molecule" and "polynucleotide" as used interchangeably herein, refer to sequences of linked nucleotides. The nucleotides may be deoxyribonucleotides or ribonucleotides, they may be standard or non-standard nucleotides; they may be modified or derivatized nucleotides; they may be synthetic analogs. The nucleotides may be linked by phosphodiester bonds or non-hydrolyzable bonds. The nucleic acid may comprise a few nucleotides (i.e., oligonucleotide), or it may comprise many nucleotides (i.e., polynucleotide). The nucleic acid may be single-stranded or double-stranded.

j) Protein and Protein Fragment

The terms "protein", "polypeptide", and "peptide" as interchangeably herein, refer to molecules composed of multiple amino acids having sequences of a variety of lengths acid including the full-length native protein or a shorter fragment of the full-length protein. These may be in neutral forms or as salts, either unmodified or modified by processes including glycosylation, side chain oxidation, and phosphorylation, or by the addition of other moieties attached to amino acid side chains, including but not limited to glycosyl units, lipids, and inorganic ions such as phosphates. Modifications may also include chemical conversion of amino acid side chains, such as oxidation of sulfhydryl groups. Molecules with such modifications are encompassed by the terms, provided that the modification(s) do not change its specific properties. It should understood that the term "protein", and its equivalents as used herein, encompasses protein isoforms encoded by the same gene that may differ in pI, MW, or both. Such isoforms may have different amino acid sequences resulting, for example, from differential processing such as alternative splicing, or post-translational modification(s). The term "protein fragment", as used herein, refers to a polypeptide comprising an amino acid sequence of at least 5 amino acid residues (preferably, at least 10 amino acid residues, at least 15 amino acid residues, at least 20 amino acid residues, at least 25 amino acid residues, at least 40 amino acid residues, at least 50 amino acid residues, at least 60 amino acid residues, at least 70 amino acid residues, at least 80 amino acid residues, at least 90 amino acid residues, at least 100 amino acid residues, at least 125 amino acid residues, at least 150 amino acid residues, at least 175 amino acid residues, at least 200 amino acid residues, or at least 250 amino acid residues) of the amino acid sequence of a second polypeptide. The fragment of a marker protein may or may not possess a functional activity of the full-length native protein.

B. Osteoarthritis Biomarkers and Arrays

The methods described herein, and diagnostic reagents, kits and related inventions disclosed herein are based in part on the surprising discovery of a plurality of molecular markers, the expression levels of which consistently differentiate between healthy subjects and subjects with OA. The same plurality of markers is able to distinguish between pre- and post-surgical OA subjects, thus also indicating that OA treatment efficacy can be evaluated with these markers. The molecular markers are genes whose altered expression in subject, as measured from a readily obtained biological sample from the subject, is indicative of the presence of OA in the subject. Also provided herein are methods of using the molecular markers to identify a candidate substance as a therapeutic substance for OA treatment, methods for determining OA treatment efficacy in a subject, and OA diagnostic reagents and kits.

As used herein, an "OA biomarker" is indicative of OA when the expression level or quantity or structure of the biomarker is found significantly more often in subjects with OA present, or having OA of the same degree, severity, type or stage, than in subjects without OA, or lacing OA of the same degree, severity, type or stage. Significance of an expression level, quantity or structure of the OA marker, as compared to a control, is determined using routine statistical methods by applying accepted confidence levels, e.g. at a minimum of 95%. It will be understood, for example, that cut-off or threshold expression levels for each OA biomarker may set according to many factors including the degree of correlation of expression level with clinical or subclinical OA indicators. For example, an expression level of a biomarker that is indicative of OA can be, for example, that found in at least 60% of patients who have the disease and is found in less than 10% of subjects who do not have the disease. More preferably, an expression level is indicative of OA if found in at least 70%, at least 75%, at least 80%, at least 85%, at least 90%, at least 95%, at least 97%, at least 98%, at least 99% or more in subjects who have the disease and is found in less than 20%, less than 10%, less than 8%, less than 5%, less than 2.5%, or less than 1% of subjects who do not have the disease.

An "OA expression profile" is any physical representation of the expression levels of a set of two or more selected OA markers, as determined from one or more biological samples from one or more subjects known to have OA, known to have OA of a particular type (subtype I or subtype II), known to have OA of a particular stage (early or late), or known to be free of OA. A profile for a particular subject or group of subjects may include expression level information from multiple types of biological samples that have been analyzed separately for OA marker expression levels. For example, an OA expression profile for a subject may include OA marker expression level information from a urine sample and a blood sample from the subject, and the results combined in a single profile representing the OA marker expression levels from both samples. A single expression profile may include expression level information from any two or more biological samples selected from synovial fluid, whole blood, blood plasma, serum, urine, and saliva, and a complete profile may include expression level information from any three or four biological samples selected from synovial fluid, urine, saliva, and whole blood, blood plasma or serum.

One skilled in the art will appreciate that the more samples from a subject that are examined, the more reliable the determination of the presence or absence, degree, severity, type or stage of OA in the subject. The profile may be represented in visual graphical form, for example on paper or on a computer display; in a three dimensional form such as an array; and/or stored in a computer-readable medium. An expression profile may correspond to a particular status of OA (e.g., presence or absence of OA disease, severity (clinical or subclinical)), type (subtype I or subtype II OA), degree (degree of cartilage damage) or stage (early OA or late OA), and thus provides a template for comparison to a patient sample. Control profiles can be obtained by analyzing a biological sample from at least one normal/healthy subject, or multiple samples obtained from a group of normal/healthy subjects, or from one or more subjects identified as having comparable OA disease in terms of severity, type or stage. Similarly, comparable profiles can be obtained for age-, sex- and body mass index-matched subjects.

The terms "normal" and "healthy" are used herein interchangeably to refer to a subject or subjects who do not display and have no history of OA symptoms such as joint pain, inflammation, or decrease in function, and have not been diagnosed with OA. A "normal" or "healthy" sample refers to a sample or samples obtained from a normal/healthy subject. A subject suspected of having OA" is a subject that exhibits one or more symptoms indicative of the presence of OA in the subject, such as but not limited to joint pain, joint swelling, and crepitus, or a subject that may be at risk of, or simply being screened for the presence of OA. Risk factors for developing OA are generally well known and include, for example, age, overweight or obesity, traumatic injury, breed, and/or family history.

An OA biomarker expression profile may for example comprise polypeptide expression level information for two or more polypeptides selected from the group consisting of: MCP1, IL8, KC, MMP2, MMP3, IL6, MMP1, RANTES, MMP9, Apolipoprotein A1, Apolipoprotein E and fragments of any thereof, and any combination thereof, obtained from a biological sample from a subject suspected of having osteoarthritis. More specifically, by analyzing samples of synovial fluid obtained from healthy patients and from patients with early OA or late OA, it has been discovered that the polypeptides listed in Table 1 discriminate between normal subjects and subjects with OA. Changes in the expression levels of these marker genes in a subject, as measured in a biological sample from subject, thus may be used to indicate the presence or absence, degree, severity, type or stage of OA on the subject. The panel of markers (see Table 1) comprises MCP1, IL8, KC, MMP2, MMP3, IL6, MMP1, RANTES, MMP9, 1L1B, Apolipoprotein A1, Apolipoprotein E, DCN, CILP and COMP. These proteins are found to be up-regulated in synovial fluid samples of subjects with early osteoarthritis compared to synovial fluid samples of normal individuals.

For example, altered expression levels of any one or more, preferably two or more of the OA markers described herein may be used to determine the presence or absence, degree, severity, type or stage of OA in one or more subjects. Altered expression of any 2, 3, 4, 5, 6, 7, 8, 9, 10, 11, 12 or more of the molecular markers may be used to determine the presence or absence, degree, severity, type or stage of OA in one or more subjects. One skilled in the art will appreciate that, generally, the more markers examined, the more accurate the determination of the presence or absence, degree, severity, type or stage of OA in the one or more subjects.

TABLE 1

OA Markers

| Official Name | Gene Name | GenBank Accession Number |
| --- | --- | --- |
| Monocyte Chemoattractant Protein-1 (MCP-1/CCL2) | CCL2 | Human G: NM_002982<br>Human P: NP_002973<br>Canine G: NM_001003297<br>Canine P: NP_001003297.1 |
| Interleukin-8 | IL8 | Human G: NM_00584<br>Human P: NP_00575<br>Canine G: NM_001003200<br>Canine P: NP_001003200 |
| Keratinocyte Chemoattractant/ GRO-alpha (CXCL1) | CXCL1 | Human G: NM_001511<br>Human P: NP_001502<br>Canine G:<br>Canine P: |
| Matrix Metalloproteinase-2 | MMP2 | Human G: NM_004530<br>Human P: NP_004521<br>Canine G: XM_535300<br>Canine P: XP_535300 |
| Matrix Metalloproteinase-3 | MMP3 | Human G: NM_002422<br>Human P: NP_002413<br>Canine G: NM_001002967<br>Canine P: NP_001002967 |
| Interleukin-6 | IL6 | Human G: NM_000600<br>Human P: NP_000591<br>Canine G: XM_850499<br>Canine P: XP_855592 |
| Matrix Metalloproteinase-1 | MMP1 | Human G: NM_002421<br>Human P: NP_002412<br>Canine G: XM_546546<br>Canine P: XP_546546 |
| RANTES, Chemokine (C-C motif) ligand 5 (CCL5 | CCL5 | Human G: NM_002985<br>Human P: NP_002976<br>Canine G: NM_001003010<br>Canine P: NP_001003010 |
| Matrix Metalloproteinase-9 | MMP9 | Human G: NM_004994<br>Human P: NP_004985<br>Canine G: NM_001003219<br>Canine P: NP_001003219 |
| Interleukin-1β | IL1B | Human G: NM_000576<br>Human P: NP_000567<br>Canine G: NM_001037971<br>Canine P: NP_001033060 |
| Apolipoprotein A1 | APOA1 | Human G: NM_000039<br>Human P: NP_000030<br>Canine G: NM_001197048<br>Canine P: XP_536564 |
| Apolipoprotein E | APOE | Human G: NM_000041<br>Human P: NP_000032<br>Canine G: XM_533644<br>Canine P: XP_533644 |

TABLE 1-continued

OA Markers

| Official Name | Gene Name | GenBank Accession Number |
| --- | --- | --- |
| Decorin | DCN | Human G: NM_001920 |
| | | Human P: NP_001911 |
| | | Canine G: NM_001003228 |
| | | Canine P: NP_001003228 |
| Cartilage Intermediate Layer Protein | CILP | Human G: NM_003613 |
| | | Human P: NP_003604 |
| | | Canine G: XM_544728 |
| | | Canine P: XP_544728 |
| Cartilage oligomeric matrix Protein | COMP | Human G: NM_000095 |
| | | Human P: NP_000086 |
| | | Canine G: XM_860228 |
| | | Canine P: XP_865321 |

Measuring the expression of any OA markers or a plurality of the OA markers may be accomplished by a variety of techniques that are well known in the art. Expression may be monitored directly by detecting products of the OA marker genes (i.e., mRNA or protein), or it may be assessed indirectly by detecting alterations in the DNA (e.g., amplification, methylation, etc.) that affect expression of the OA marker genes. RNA, protein, or DNA may be isolated from cells of interest using techniques well known in the art and disclosed in standard molecular biology reference books, such as Ausubel et al., (2003) CURRENT PROTOCOLS IN MOLECULAR BIOLOGY, John Wiley & Sons, New York, N.Y.

Detection of the RNA products of the OA marker genes may be accomplished by a variety of methods. Some methods are quantitative and allow estimation of the original levels of RNA between the OA sample and control sample, whereas other methods are merely qualitative. Additional information regarding the methods presented below may be found for example in Ausubel et al., (2003) CURRENT PROTOCOLS IN MOLECULAR BIOLOGY, John Wiley & Sons, New York, N.Y., or Sambrook et al. (1989) MOLECULAR CLONING: A LABORATORY MANUAL, Cold Spring Harbor Press, Cold Spring Harbor, N.Y. A person skilled in the art will know which parameters may be manipulated to optimize detection of the mRNA of interest.

Quantitative real-time PCR (QRT-PCR) may be used to measure the differential expression of any OA marker in an OA sample and control sample. In QRT-PCR, the RNA template is generally reverse transcribed into cDNA, which is then amplified via a PCR reaction. The PCR amplification process is catalyzed by a thermostable DNA polymerase. Non-limiting examples of suitable thermostable DNA polymerases include Taq DNA polymerase, Pfu DNA polymerase, Tli (also known as Vent) DNA polymerase, Tfl DNA polymerase, and Tth DNA polymerase. The PCR process may comprise three steps (i.e., denaturation, annealing, and extension) or two steps (i.e., denaturation and annealing/extension). The temperature of the annealing or annealing/extension step can and will vary, depending upon the amplification primers. That is, their nucleotide sequences, melting temperatures, and/or concentrations. The temperature of the annealing or annealing/extending step may range from about 50° C. to about 75° C. The amount of PCR product is followed cycle-by-cycle in real time, which allows for determination of the initial concentrations of mRNA. The reaction may be performed in the presence of a dye that binds to double-stranded DNA, such as SYBR Green. The reaction may also be performed with fluorescent reporter probes, such as TAQMAN® probes (Applied Biosystems, Foster City, Calif.) that fluoresce when the quencher is removed during the PCR extension cycle. Fluorescence values are recorded during each cycle and represent the amount of product amplified to that point in the amplification reaction. The cycle when the fluorescent signal is first recorded as statistically significant is the threshold cycle (Ct). To minimize errors and reduce any sample-to-sample variation, QRT-PCR is typically performed using an internal standard. The ideal internal standard is expressed at a constant level among different tissues, and is unaffected by the experimental treatment. Suitable internal standards include, but are not limited to, mRNAs for the housekeeping genes glyceraldehyde-3-phosphate-dehydrogenase (GAPDH) and beta-actin.

Reverse-transcriptase PCR (RT-PCR) may also be used to measure the differential expression of an OA marker. As described above, the RNA template is reverse transcribed into cDNA, which is then amplified via a typical PCR reaction. After a set number of cycles the amplified DNA products are typically separated by gel electrophoresis. Comparison of the relative amount of PCR product amplified in the different cells will reveal whether the molecular marker is differentially expressed in an OA sample.

Differential expression of an OA marker may also be measured using a nucleic acid microarray. In this method, single-stranded nucleic acids (e.g., cDNAs, oligonucleotides, etc.) are plated, or arrayed, on a solid support. The solid support may be a material such as glass, silica-based, silicon-based, a synthetic polymer, a biological polymer, a copolymer, a metal, or a membrane. The form or shape of the solid support may vary, depending on the application. Suitable examples include, but are not limited to, slides, strips, plates, wells, microparticles, fibers (such as optical fibers), gels, and combinations thereof. The arrayed immobilized sequences are generally hybridized with specific DNA probes from the cells of interest. Fluorescently labeled cDNA probes may be generated through incorporation of fluorescently labeled deoxynucleotides by reverse transcription of RNA extracted from the cells of interest. The probes are hybridized to the immobilized nucleic acids on the microchip under highly stringent conditions. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified molecular marker is thus determined simultaneously. Microarray analysis may be performed by commercially available equipment, following manufacturer's protocols, such as by using the Affymetrix GenChip technology, or Incyte's microarray technology.

Differential expression of an OA marker may also be measured using Northern blotting. For this, RNA samples are first separated by size via electrophoresis in an agarose gel under denaturing conditions. The RNA is then transferred to a membrane, crosslinked, and hybridized, under highly stringent conditions, to a labeled DNA probe. After washing to remove the non-specifically bound probe, the hybridized labeled species are detected using techniques well known in the art. The probe may be labeled with a radioactive element, a chemical that fluoresce when exposed to ultraviolet light, a tag that is detected with an antibody, or an enzyme that catalyses the formation of a colored or a fluorescent product. A comparison of the relative amounts of RNA detected in a control sample and a test sample will reveal whether the expression of the OA marker or OA markers is changed in the test sample.

Nuclease protection assays may also be used to monitor the differential expression of an OA marker in an OA sample and control sample. In nuclease protection assays, an antisense probe hybridizes in solution to an RNA sample. The antisense probe may be labeled with an isotope, a fluorophore, an enzyme, or another tag. Following hybridization, nucleases are added to degrade the single-stranded, unhybridized probe and RNA. An acrylamide gel is used to separate the remaining protected double-stranded fragments, which are then detected using techniques well known in the art. Again, qualitative differences in expression may be detected.

Differential expression of an OA marker may also be measured using in situ hybridization. This type of hybridization uses a labeled antisense probe to localize a particular mRNA in cells of a tissue section. The hybridization and washing steps are generally performed under highly stringent conditions. The probe may be labeled with a fluorophore or a small tag (such as biotin or digoxigenin) that may be detected by another protein or antibody, such that the labeled hybrid may be visualized under a microscope. The transcripts of an OA marker may be localized to the nucleus, the cytoplasm, or the plasma membrane of a cell.

Detection of the protein products of the OA markers may be accomplished by several different techniques, many of which are antibody-based. Additional information regarding the methods discussed below may be found in Ausubel et al., (2003) CURRENT PROTOCOLS IN MOLECULAR BIOLOGY, John Wiley & Sons, New York, N.Y., or Sambrook et al. (1989) MOLECULAR CLONING: A LABORATORY MANUAL, Cold Spring Harbor Press, Cold Spring Harbor, N.Y. One skilled in the art will know which parameters may be manipulated to optimize detection of the protein of interest.

An enzyme-linked immunosorbent assay (ELISA) may be used to detect and quantify protein levels. This method comprises preparing the antigen (i.e., protein of interest), coating the wells of a microtiter plate with the antigen, incubating with an antibody that recognizes the antigen, washing away the unbound antibody, and detecting the antibody-antigen complex. The antibody is generally conjugated to an enzyme, such as horseradish peroxidase or alkaline phosphatase, which generate colorimetric, fluorescent, or chemiluminescent products. An ELISA may also use two antibodies, one of which is specific to the protein of interest and the other of which recognizes the first antibody and is coupled to an enzyme for detection. Further, instead of coating the well with the antigen, the antibody may be coated on the well. In this case, a second antibody conjugated to a detectable compound is added following the addition of the antigen of interest to the coated well.

The Luminex platform (available from Luminex Corp., Austin, Tex.) can be used to detect and quantify protein levels using multiplexed assays based on a capture bead system in which microsphere beads are color-coded with dyes into up to one hundred distinct sets. Each color-coded bead set is coated with a specific binding reagent such as an antibody specific to a selected protein marker, allowing the capture and detection of specific protein analytes from a very small amount, e.g. a drop of fluid, from a biological sample such as plasma, serum, lysates or synovial fluid. Depending upon which analyte(s) are being screened, at least one or several bead sets may be incubated with the sample in order to capture the analytes. A Luminex compact analyzer uses lasers to excite the internal dyes that identify each microsphere beads, and also any reporter dye captured during the assay. Multiple readings can be made on each bead set. Because of the special dye ratio incorporated each bead, each unique bead population can be analyzed separately after acquisition. An exemplary multiplex immunoassay platform is also the xMAP platform available from Qiagen Inc.

Relative protein levels may also be measured by Western blotting. Western blotting generally comprises preparing protein samples, using gel electrophoresis to separate the denatured proteins by mass, and probing the blot with antibodies specific to the protein of interest. Detection is usually accomplished using two antibodies, the second of which is conjugated to an enzyme for detection or another reporter molecule. Methods used to detect differences in protein levels include colorimetric detection, chemiluminescent detection, fluorescent detection, and radioactive detection.

Measurement of protein levels may also be performed using a protein microarray or an antibody microarray. In these methods, the proteins or antibodies are covalently attached to the surface of the microarray or biochip. The protein of interest is detected by interaction with an antibody, and the antibody/antigen complexes are generally detected via fluorescent tags on the antibody.

Relative protein levels may also be assessed by immunohistochemistry, in which a protein is localized in cells of a tissue section by its interaction with a specific antibody. The antigen/antibody complex may be visualized by a variety of methods. One or two antibodies may be used, as described above for ELISA. The detection antibody may be tagged with a fluorophore, or it may be conjugated to an enzyme that catalyzes the production of a detectable product. The labeled complex is typically visualized under a microscope.

Changes in the expression of any one or more OA markers may also be assessed by detecting alterations in the DNA encoding each OA marker gene. The DNA may be amplified, which is a process whereby the number of copies of a region of DNA or a gene is increased. Usually, the amount of RNA product is also increased, in proportion to the number of additional copies of DNA. Amplification of DNA may be detected by PCR techniques, which are well known in the art. Amplification of DNA may also be detected by Southern blotting, in which genomic DNA is hybridized to labeled probes under highly stringent conditions, and the labeled hybrids may be detected as described above for Northern blotting.

Changes in the methylation status of DNA may also indicate changes in expression of any OA marker. The regulatory region of a gene may be methylated, which entails the addition of a methyl group to the 5-carbon of cytosine in a CpG dinucleotide. Genes that are transcriptionally silent tend to have methylated or hypermethylated regulatory regions. Thus, demethylation of an OA marker gene may lead to increased expression in tissue or cells, which is detectable from a biological sample obtained from a subject. Likewise, methylation of an OA marker gene may lead to decreased expression in issue or cells, which is detectable from a biological sample obtained from a subject. Changes in the methylation status of an OA marker gene in a sample or samples from one or more subjects with OA, relative to a sample or samples from one or more control subjects, may be assessed using methylation-sensitive restriction enzymes to digest DNA followed by Southern detection or PCR amplification. Changes in the methylation status of an OA marker may also be detected using a bisulfite reaction based method. For this, sodium bisulfite is used to convert unmethylated cytosines to uracils, and then the methylated cytosines are detected by methylation specific PCR (MSP).

Single nucleotide polymorphisms (SNPs) in the regulatory region of an OA marker gene may also affect its level of expression. For example, an altered nucleotide may affect the binding of a transcription factor such that transcription is up-regulated or down-regulated. The presence of a particular SNP may be detected by DNA sequencing. A SNP may also be detected by selective hybridization to an oligonucleotide probe (i. e., it hybridizes to a sequence containing a particular SNP, but not to sequences without the SNP). A particular SNP may also be detected using a PCR based technique or an oligonucleotide microarray based assay.

Expression of any one or more of the OA markers can be measured in an OA sample relative to a control sample. The OA cell may be isolated from a subject known to have OA based on generally accepted clinical indicators, and expression of any OA marker may be examined in vitro. The type of biopsy used to isolated cells can and will vary, depending upon the location and nature of the OA. A sample of cells, tissue, or biological fluid such as synovial fluid, may be removed by needle aspiration biopsy. For this, a fine needle attached to a syringe is inserted through the skin and into the organ, tissue or joint capsule of interest. The needle may be guided to the region of interest using ultrasound or computed tomography (CT) imaging. Once the needle is inserted into the tissue, a vacuum is created with the syringe such that cells or fluid may be sucked through the needle and collected in the syringe. A sample of cells or tissue may also be removed by incisional or core biopsy. For this, a cone, a cylinder, or a tiny bit of tissue is removed from the region of interest. This type of biopsy is generally guided by CT imaging, ultrasound, or an endoscope.

RNA, protein, or DNA may be extracted from any biological sample containing cells or tissue, to permit analysis of the expression level or levels of any one or more OA markers using methods described herein above. Biopsied cells or tissue may also be embedded in plastic or paraffin, from which nucleic acids may be isolated. The expression of an OA marker may also be performed in the biopsied cells or tissue in situ (e.g., in situ hybridization, immunohistochemistry).

Expression of an OA marker may also be examined in vivo in a subject. A particular mRNA or protein may be labeled with fluorescent dye, a bioluminescent marker, a fluorescent semiconductor nanocrystal, or a short-lived radioisotope, and then the subject may be imaged or scanned using a variety of techniques, depending upon the type of label.

C. Methods

A method for diagnosing, staging, or monitoring osteoarthritis can include, for example, measuring in a biological sample from the subject the level of expression of at least two polypeptides selected from the group consisting of: MCP1, IL8, KC, MMP2, MMP3, MMP9, IL6, MMP1, RANTES, IL1B, Apolipoprotein A1, Apolipoprotein E, DCN, CILP and COMP, and fragments of any thereof, and any combination thereof, wherein the expression levels of the at least two polypeptides or fragments thereof in the biological sample provide a sample protein expression profile indicative of the presence or absence, degree, severity, type or stage of osteoarthritis in the subject. The level of expression of the at least two polypeptides is measured using any of the above protein or nucleic acid quantification techniques, including but not limited to by detecting alterations in DNA due to a process selected from the group consisting of DNA amplification, DNA methylation/demethylation, and single nucleotide polymorphisms.

The method may further comprise comparing the sample protein expression profile to a control protein expression profile, wherein a difference between the sample protein expression profile and the control protein expression profile is indicative of the presence or absence, degree, severity, type or stage of osteoarthritis in the subject. The OA biomarkers described herein are thus used in methods to detect the presence of OA in a subject, to study populations of subjects as to the occurrence of OA, and to evaluate OA treatment efficacy. Accordingly, the present disclosure provides methods for characterizing test samples obtained from a subject suspected of having OA, for diagnosing OA in a subject, for identifying the subtype of OA, and for assessing the advancement of OA in a subject. In such methods, the biomarkers' expression levels determined for a biological sample obtained from the subject are compared to the levels in one or more control samples. The control samples may be obtained from a healthy subject (or a group of healthy subjects), from a subject (or group of subjects) with OA, from a subject (or group of subjects) with subtype I OA or subtype II OA, and/or from an subject (or group of subjects) with a specific stage of the disease (e.g., early OA or late OA). As mentioned above, the control expression levels of the biomarkers of interest are preferably determined from a significant number of individuals, and an average or mean is obtained. In certain preferred embodiments, the expression levels determined for the biological sample under investigation are compared to at least one expression profile for OA, as described above.

The OA biomarkers having expression levels that correlate with the presence or absence of OA, or OA degree, severity, type or stage, are attractive targets for the identification of new therapeutic agents (e.g., using screens to detect compounds or substances that inhibit or enhance the expression of these biomarkers). Accordingly, the present disclosure also provides methods for the identification of compounds or substances with the potential for effectively treating OA, or slowing OA progression.

The OA biomarkers can be readily applied in various screening methods, for example for identifying a candidate substance as a therapeutic agent for treating osteoarthritis. Such a method may comprise, for example, a) administering the candidate substance to a subject diagnosed with spontaneous osteoarthritis; b) measuring the expression level of two or more OA polypeptides selected from the group consisting of MCP1, IL8, KC, MMP2, MMP3, IL6, MMP1, RANTES, MMP9, IL1B, Apolipoprotein A1, Apolipoprotein E, DCN, CILP and COMP in a biological sample from the subject; and c) selecting the candidate substance as a candidate therapeutic agent for treating osteoarthritis if the expression level of each of the two or more OA polypeptides in the biological sample is lower than or equal to the expression level for the selected two or more OA polypeptides in a biological sample from a control subject not administered the test substance.

The methods may further include, for example, contacting a biological system that expresses at least one OA biomarker, with a candidate (test) substance for a time and under conditions sufficient for the candidate substance to change the expression of the at least one OA biomarker, and measuring a first OA biomarker expression level. The method may further comprise maintaining the biological system for the same time and under the same conditions in the absence of the candidate substance, or after contacting the biological system with a control substance, then measuring a second OA biomarker expression level; and comparing the first and second OA biomarker expression levels, wherein a first OA biomarker expression level that is less than or greater than the second OA biomarker expression level is indicative that the candidate substance is a candidate therapeutic agent for treating OA. Any candidate substance or a plurality of substances (e.g. a library) can be screened, including but not limited to synthetic and natural substances, and any combination of naturally occurring and synthetic substances. It should be understood that such screening can be performed using multiple OA biomarkers in parallel, which may be facilitated using any of many readily commercially available multiplex assays. The method may further include generating an OA expression profile for the one or more OA biomarkers being evaluated, which can include for example expression information for each OA biomarker under the test and control conditions.

Such screening methods may be carried out using any type of biological system, such as but not limited to a cell or cells, a biological fluid, a biological tissue, or an animal. Methods can be carried out using any system capable of showing cartilage degeneration in response to the presence of induced or spontaneously occurring OA, including but not limited to an animal model, a whole body part such as a knee, hip or elbow, or a portion thereof. Assay and screening methods can be performed using cells grown in standard tissue culture. Preferably, such cells are mammalian, and more preferably of canine or human origin. Cells may be primary cells, secondary cells, or immortalized cells and can be prepared by techniques well known in the art, including cells that are genetically engineered to contain or knock out a selected gene, or are available from well known commercial sources such as the American Type Culture Collection, Manassas, Va. Those of routine skill in the art can select a cell type or cell line according to generally recognized principles such as the objective of the assay, type and number of OA marker, drug being tested, and the like. Cells may be cultured using standard cell culture techniques, media and standards, such as growing and maintaining in a sterile environment at 37° C.

Any candidate substance identified by the screening methods can be further tested in assays that allow for the determination of the compound's properties in vivo. Suitable animal models of osteoarthritis are well known in the art, including models of spontaneously occurring OA and OA induced by surgical instability or genetic modification. Animal models of naturally occurring OA occur in knee joints of guinea pigs, mice, and Syrian hamsters. Models of OA induced by surgical instability include medial meniscal tear in guinea pigs and rats, medial or lateral partial meniscectomy in rabbits, and medial partial or total meniscectomy or anterior cruciate transection in dogs. Transgenic mouse models are known. Other animal models of OA that can be used for validating a candidate substance identified as a potential OA therapeutic agents include many others described in detail in the literature known to those in the art. Alternatively, the OA biomarkers can be applied in a method for monitoring the effect of a treatment of osteoarthritis in a subject. Such a method may comprise, for example, a) obtaining a first OA biomarker expression profile comprising measuring the expression level of two or more OA polypeptides selected from the group consisting of MCP1, IL8, KC, MMP2, MMP3, IL6, MMP1, RANTES, MMP9, IL1B, Apolipoprotein A1, Apolipoprotein E, DCN, CILP and COMP in a first biological sample obtained from the subject before the osteoarthritis treatment is administered to the subject; b) obtaining a second OA biomarker expression profile comprising measuring the expression level of the two or more OA polypeptides selected in (a), in a second biological sample obtained from the subject after or while the osteoarthritis treatment is administered to the subject; and c) comparing the first OA biomarker expression profile with the second OA biomarker expression profile, wherein if the expression level of each of the two or more selected OA polypeptides in the first OA biomarker expression profile is lower than or equal to the expression level for the selected two or more OA polypeptides in the second biological sample from the subject is indicative of a therapeutic effect of the osteoarthritis treatment in the subject.

The terms "OA treatment" and "osteoarthritis treatment" as used interchangeably herein, refer to the application of, or administration of any therapeutic device or agent that reduces the expression levels in a subject of any combination of two or more of the OA biomarkers described therein, and/or that reduces or eliminates clinical symptoms of OA in a subject.

Once the responsiveness of a subject to a particular OA treatment has been determined, an effective treatment may be selected for treating a subject with OA. If for example the OA is determined to be responsive to a particular pharmaceutical agent, then a treatment comprising the agent may be given to the subject. If, however, the OA is determined to be non-responsive to the agent, then another treatment may be selected for the subject. Thus, determining the responsiveness of a subject before administering a treatment regime would spare subjects from potentially toxic or unhelpful treatments. Route of administration for any agent that is a candidate substance for treating OA will vary depending upon factors including the nature of the agent. The route of administration may be intradermal, transdermal, parenteral, intravenous, intramuscular, intranasal, subcutaneous, percutaneous, intratracheal, intraperitoneal, intratumoral, oral, perfusion, lavage, or direct injection. The treatment regimen can and will vary, depending on the type of OA, its location, its stage, and the health and age of the subject.

D. Reagents and Kits

Kits according to the present disclosure may comprise one or more reagents for measuring the expression of at least one OA marker, wherein changes in the expression of the one or more OA in a subject relative to a control subject are indicative of the presence or absence, stage, severity or subtype of OA. OA markers comprise those listed in Table 1. A diagnostic kit may include at least one reagent that is capable of specifically binding to at least one OA marker as described herein, to thereby detect the expression level of one or more of the OA markers.

Each kit may comprise one or more specific binding reagents, each binding reagent specific to a selected OA marker or fragment thereof. The specific binding reagents may each comprise any molecule capable of such specific binding, such as an antibody that specifically binds to the protein marker, or fragment thereof, or a nucleic acid probe complementary to a polynucleotide sequence such as a cDNA or oligonucleotide. By "specific binding" is meant the reaction of the reagent with the polypeptide to produce a detectable product, while not reacting detectably with other polypeptides having unrelated sequences. Specific binding reagents to be used in the measurement of the expression of the OA markers can and will vary, depending upon the type of technique to be used. For example, the kit may comprise oligonucleotide primers for QRT-PCR. Nucleic acid probes contained may be included in a kit and are optionally provided together with a solid substrate, such as but not limited to beads, a chip, a plate, and a microarray. Nucleic acid probes are optionally immobilized on the surface of such a substrate. The kit may comprise fluorescent reporter probes. The kit may also further comprise a reverse transcriptase, a Taq polymerase, and appropriate buffers and salts.

A kit may comprise antibodies that can be used for an immunoassay, e.g. for an ELISA. The kit may further comprise a substrate for detection of enzyme-conjugated antibodies. Antibodies that can be used in the methods and included in kits include monoclonal and polyclonal antibodies, immunologically active fragments (e.g., Fab or (Fab) 2 fragments), antibody heavy chains, humanized antibodies, antibody light chains, and chimeric antibodies. Antibodies, including monoclonal and polyclonal antibodies, fragments and chimeras, may be prepared and purified using methods well known in the art, or obtained from scientific or commercial sources. Any binding agent can be directly or indirectly labeled with a detectable label.

Preferably, the detectable label generates a signal that can be measured and is correlated, e.g. proportional to the amount of protein marker present in the sample being analyzed. Detectable labels, methods for labeling molecules including polypeptides, antibodies and oligonucleotides are well-known in the art.

Additional reagents useful for analyzing biological samples, for example determining the presence or absence, degree, severity, type or stage of OA in a subject, may be provided in a kit. Depending on the technique or procedure, the kit may further comprise one or more additional reagents such as, but not limited to, buffers such as extraction buffers, amplification buffers, hybridization buffers, immunodetection buffers, labeling buffers, or any equivalent reagent. Reagents may be supplied in solid (e.g., lyophilized) or liquid form, and these may optionally be provided in individual packages using containers such as vials, packets, bottles and the like, for each individual reagent. Each component can for example be provided in an amount appropriate for direct use or may be provided in a reduced or concentrated form that can be reconstituted. Diagnostic and treatment monitoring kits can further comprise materials and tools useful for carrying out diagnostic and monitoring methods according to the present disclosure. The kits can be used for example in diagnostic laboratories, clinical or research settings. The kit may further comprise instructions for use, including for example any procedural protocols and instructions for using the various reagents in the kit for performing different steps of the process. Instructions for using the kit according to one or more methods of the invention may comprise instructions for processing the biological sample obtained from the subject and/or for performing the test, and instructions for analyzing or interpreting the results. Instructions may be provided in printed form or stored on any computer readable medium including but not limited to DVDs, CDs, hard disk drives, magnetic tape and servers capable of communicating over computer networks.

A kit may further comprise one or more control samples. A kit may comprise at least one expression profile for OA, OA subtype, and/or OA progression as described herein for use as comparison template. Preferably, the expression profile is provided as digital information stored on a computer-readable medium.

It will be understood that generally, components of a kit are conveniently packaged or bound together for ease of handling in commercial distribution and sale.

E. Adaptations of the Methods of the Present Disclosure

By way of example, and not of limitation, examples of the present disclosures shall now be given.

Example 1

Assessment of Proteins in Media from In Vitro Cultured Normal and OA Articular Cartilage Explants Articular cartilage was harvested from the femoral head of dogs (n=6) undergoing total hip replacement due to chronic OA and from dogs (n=6) with no overt clinical signs of OA and euthanized for reasons unrelated to the present study. Two 4 mm explants were created from the tissue of each animal and incubated in 500 ul of DMEM with supplemental nutrients for 7 days. Culture media from each individual was analyzed using a canine cytokine and chemokine immunoassay for MCP1, IL-8 and KC (Millipore) based on the xMAP platform. A second aliquot was analyzed using a multiplex human MMP immunoassay for MMPs 2, 3 and 13 (R&D Systems) that has been shown to cross react with canine samples. Clinically relevant subgroups were then created based on OA-status and the media from each subgroup was pooled for proteomics analysis. Each media pool was acetone precipitated and quantified to ensure equivalent protein loading for one-dimensional polyacrylamide gel electrophoresis (1D-PAGE) with reducing conditions. Gel separation of the normal group could not be pursued due to insufficient volume and very low protein concentration of the normal culture media. Following gel separation of the remaining pooled samples, each lane was cut into 8 equal sections (total n=24) and in-gel trypsin digests were performed. Each digest was analyzed by LC-MS/MS using LTQ Orbitrap instrumentation. Results were statistically evaluated with the unpaired t-test with significance set at $p<0.05$. Following initial analysis, high abundance blood proteins were "hidden" from the instrument and re-analysis of the subclinical OA and clinical OA was performed. Fold changes between these two groups were determined using the Scaffold 2 Viewer Proteome software.

Subclinical OA versus Clinical OA (mild and severe): Alterations of 57 proteins were identified in media between subclinical OA and clinical OA groups, including numerous high abundance blood proteins (serum albumin) and several extracellular matrix (ECM) proteins. Cartilage Oligomeric Matrix Protein (COMP) was significantly higher in the subclinical OA group compared to clinical OA groups ($p=0.0033$).

Figure 1B:
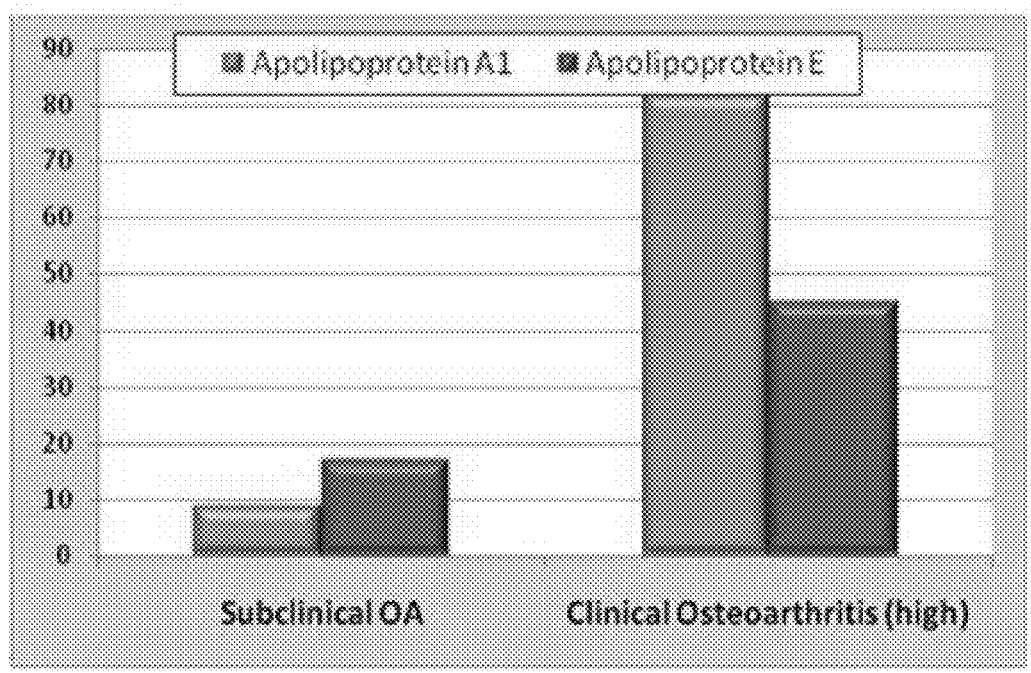
FIG. 1B is a bar graph showing levels (Mean±SE concentrations (pg/ml)), of Apolipoprotein A1 and Apolipoprotein E in dogs with subclinical OA and in dogs with clinical OA following removal of high abundance proteins.

Subclinical OA versus Severe Clinical OA (FIG. 1): The bar graphs show quantitative values obtained by Mass-Spec for select proteins from subclinical OA and clinical OA (high) groups following the removal of high abundance blood proteins. Alterations of 155 proteins were identified in media between subclinical OA and severe clinical OA groups once high abundance proteins were masked. Cartilage Intermediate Layer Protein (CILP), Decorin and COMP were all lower in the severe clinical OA group [4.2×, 4.0× and 1.4× respectively] (FIG. 1A). Apolipoproteins A1 and E were 9.1× and 2.6× higher in the severe clinical OA group, respectively (FIG. 1B).

Removal of high abundance proteins, such as albumin, greatly increased the detection of lower abundance proteins in this study. COMP is currently one of the most studied biomarkers in joint disease, and it has been shown to be significantly increased during the initial stages of OA followed by a decline in the later stages of disease. COMP was higher in the dogs in the subclinical OA group in this study, thus providing additional support for the use of this novel biomarker panel for the diagnosis of early OA. Another protein of interest is Apolipoprotein A1 (ApoA1). ApoA1 has been shown to be higher in osteoarthritic canine and human synovial fluid and human articular cartilage compared to normal, but to our knowledge we are the first to confirm the release of ApoA1 from canine articular cartilage. These results provide continued support for the use of canine tissues in translational research for human OA, and additional support for the use of a biomarker panel for diagnosis and staging of early OA.

Further study was undertaken to: 1) delineate the alterations of cytokine and chemokine concentrations in synovial fluid in osteoarthritic and non-osteoarthritic knee joints and 2) determine if any cytokine and chemokine fluctuations discern OA using receiver operating characteristic (ROC) curve analysis. Twenty-one adult, intact female, hound dogs >20 kg were included in this study. Each dog underwent one of four arthroscopic procedures: transection of the anterior cruciate ligament (ACL-T), transection of the meniscus (MR), creation of two full-thickness grooves in the cartilage of the medial femoral condyle (Groove) or probe manipulation of all joint landmarks without insult (SHAM). The non-operated, contralateral hind limb served as an internal control for each dog. Synovial fluid was collected immediately prior to surgery on the operated limb, and 12 weeks post-operatively from both the operated and contralateral control limbs. These were analyzed using a multiplex canine cytokine and chemokine immunoassay (Millipore) for IL-2, IL-4, IL-7, IL-8, IL-15, IL-18, IP-10, INF-γ, TNF-α, MCP1, KC, and GM-CSF based on the xMAP platform. Results were statistically evaluated with the unpaired t-test or the Mann-Whitney Rank Sum test with significance set at p<0.05. Imaging studies (including ultrasound and magnetic resonance imaging), arthroscopy and histopathologic data were also collected to fully characterize the pathology of all joint tissues.

In the synovial fluid, monocyte chemoattractant protein 1 (MCP1) was significantly increased in ACL-T joints (n=5) 12 weeks after surgery compared to day 0 (n=21; p<0.001) and the SHAM joints at 12 weeks (n=5; p<0.009). Increased MCP1 was also observed in the Groove (n=6) and MR groups (n=5) at 12 weeks compared to day 0, but statistical significance was not reached. Interleukin-8 (IL-8) was significantly increased at 12 weeks in the ACL-T and MR dogs compared to day 0 (n=21; A: p=0.001, M: p=0.018), the non-operated limb at 12 weeks (n=21; A: p=0.002, M: p=0.018), and the SHAM group (n=3; A: p=0.019, M: p=0.049) at 12 weeks. Keratinocyte-derived chemoattractant (KC) was significantly decreased in the Groove group at 12 weeks (n=6) compared to day 0 (n=21; p=0.009). The remaining cytokines and chemokines were below detectable levels in the synovial fluid of these animals. Using receiver operating characteristic curves, areas under the curve (AUC) were calculated for IL-8, MCP1 and KC individually and as a combined panel (Table 2).

TABLE 2

Areas under the curve (AUC) ± SE for IL-8, KC or MCP1

|  | ACL-T vs SHAM | OA vs SHAM |
|---|---|---|
| IL-8 | 1 | 0.86 ± 0.07 |
| MCP1 | 0.67 ± 0.17 | 0.59 ± 0.17 |
| KC | 0.74 ± 0.17 | 0.62 ± 0.17 |
| Combined |  | 0.88 ± .11 |

Thus in canine models of OA, changes in cytokine and chemokine levels occur within the synovial fluid after OA induction. ROC curves for diagnostic tests with perfect discrimination between normal and OA have an AUC=1.0. The results demonstrated that a biomarker panel including monocyte chemoattractant protein 1 (MCP1/CCL2), interleukin-8 (IL-8/CXCL8) and keratinocyte-derived chemoattractant (KC/CXCL1) demonstrates strong discriminatory ability for distinguishing OA dogs from normal dogs.

Example 2

Assessment of Synovial Fluid and Serum Cytokines, Chemokines and Matrix Metalloproteinases (MMPs) in Dogs with Spontaneously Occurring OA Methods: Informed client consent was obtained for each dog included in this study. Blood and synovial fluid were obtained from 10 adult medium and large breed dogs presenting to the UMC-VMTH for surgical intervention of unilateral stifle (knee) OA (Pre-Op OA; n=10). These dogs ranged from 3-8 years old (mean 5.15 years median might be better). Synovial fluid was obtained from the affected stifle via routine aseptic arthrocentesis, and blood was collected via jugular venipuncture. Clinical knee OA was confirmed in each dog by a board-certified veterinary orthopedic surgeon. Radiographic evidence of OA was confirmed by a board-certified veterinary radiologist. All dogs underwent knee surgery for cruciate ligament deficiency and recovered uneventfully. Eight to 12 weeks later, the dogs returned for a postoperative re-check, and blood and synovial fluid were collected again to assess changes in markers after surgical intervention. The control group was comprised of nine medium and large breed adult dogs ranging from 2-5 years old (mean 2.9 years). These dogs had no clinical history of joint trauma, were not lame and were deemed to be free of clinical OA by a board certified veterinary orthopedic surgeon. Radiographic evaluation of the shoulders, knees and hips verified the absence of OA. Blood and synovial fluid were collected in a similar manner to the OA dogs at a time convenient to the clients. The synovial fluid samples were analyzed in duplicate using a multiplex canine cytokine and chemokine immunoassay (Millipore Corp. St. Louis, Mo., USA) based on the xMAP platform (Qiagen Inc.) for IL-2, IL-4, IL-6, IL-7, IL-8, IL-10, IL-15, IL-18, IP-10, INF-γ, TNF-α, MCP1, KC, and GM-CSF per manufacturers' instructions. Another 25 μls was analyzed in duplicate using a multiplex human matrix metalloproteinase (MMP) immunoassay (R&D Systems, Minneapolis, Minn., USA) based on the xMAP platform (Qiagen, Inc.) for MMP1, MMP2, MMP3, MMP9 and MMP13. This assay has been previously shown by our laboratory to cross-react with samples of canine origin. Results were statistically evaluated with an unpaired t-test or Mann-Whitney Rank Sum test (SigmaStat 3.5; Systat Software, Incorporated, San Jose, Calif., USA) with significance set at p<0.05. Results:

Results obtained following the methods described above are summarized in FIGS. 2A and 2B and Table 3 (below).

TABLE 3

Proteins exhibiting differences in expression between synovial fluid collected from normal and OA canine knees

| SYNOVIAL FLUID Identified Protein | FOLD CHANGE Normal: OA |
|---|---|
| Aggrecan core protein | 2.08 |
| Clusterin | 0.3 |
| Alpha-2-macroglobulin | 0.22 |
| Angiotensinogen | 0.41 |
| Apolipoprotein B-100 | 0.13 |
| Complement C3 | 0.4 |
| Complement factor J | 0.43 |
| Fibronectin 1 isoform 1 preproprotein | 0.32 |
| Transthyretin | 3.25 |
| Zinc-alpha-2-glycoprotein | 0.21 |

Figure 2A:
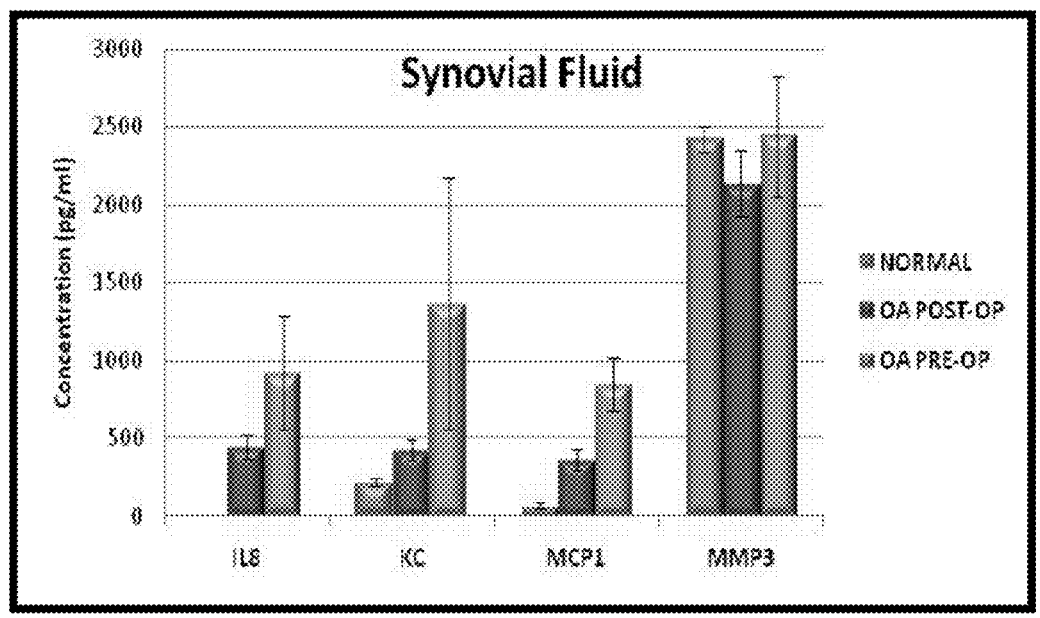
FIG. 2A is a bar graph showing levels (Mean±SE concentrations (pg/ml)), of IL8, KC, MCP1 and MMP3 in normal dogs and in dogs with spontaneous knee OA before and after 10 surgery.
Figure 2B:
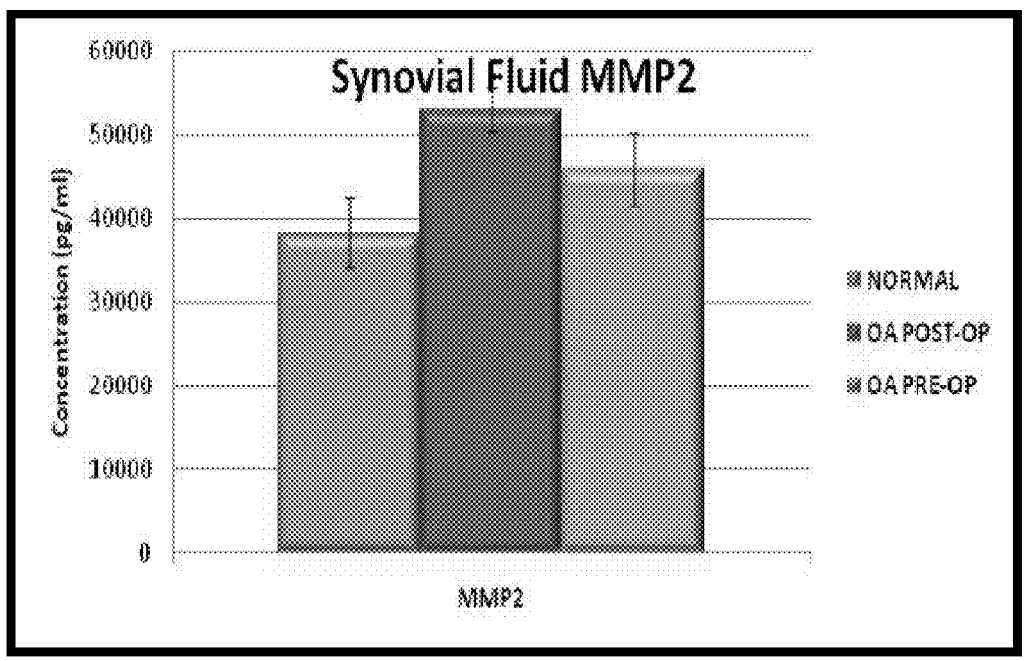
FIG. 2B is a bar graph showing levels (Mean±SE concentrations (pg/ml)), of MMP2 in normal dogs and in dogs with spontaneous knee OA before and after surgery.

In synovial fluid, IL8 and KC were significantly higher in the Pre-Op OA dogs compared to normal dogs (p<0.001; p=0.01) and in the Post-Op OA dogs compared to normal dogs (p=0.002; p=0.03). Both analytes were lower in Post-Op OA dogs compared to Pre-Op OA dogs, but this decrease was not statistically significant. MCP-1 was significantly higher in the Pre-Op OA dogs and Post-Op OA dogs compared to normal dogs (p<0.001; P=0.009), and there was a significant decrease in MCP-1 following surgery compared to pre-surgery values (p=0.01). IL8 was significantly higher in the Pre-Op OA dogs compared to normal dogs (p=0.02), but the remaining cytokines and chemokines were below the limit of detection. MMP2 was highest in the Post-Op OA dogs, and this was significantly higher than the normal dogs (p=0.010). MMP3 was highest in the Pre-Op OA dogs and lowest in the Post-Op OA dogs, but these changes did not reach statistical significance. (FIGS. 2A and 2B). The performances of these markers as individuals and as a combined panel were evaluated through ROC curve analysis using statistical software (SAS Institute). Specifically, ROC curves were generated using JMP 7.0.2 software (SAS Institute) and used to determine the discriminatory abilities of the various biomarker combinations. Several biomarker panels led to perfect discrimination (AUC=1.0) between groups (Table 4). In Table 4, "Cyto Markers" are IL8, MCP1 and KC, and "Cyto and MMP" refers to IL8, MCP1, KC, MMP2 and MMP3.

TABLE 4

Analyte panels that lead to perfect AUCs

| | Area Under the Curves | |
|---|---|---|
| Comparison | Cyto markers | Cyto and MMP |
| Normal vs Pre-surgical OA | 1 | 1 |
| Normal vs Post-surgical OA | 1 | 1 |
| Pre-surgical vs Post-surgical OA | | 1 |
| Normal vs OA | 1 | |

The remaining serum and SF were separated with 1D-PAGE and analyzed by liquid chromatography mass spectrometry (LC-MS/MS). Matches were searched against the National Center for Biotechnology Information (NCBI) non-redundant database taxonomy-limited to dogs only. Significant differences between groups were represented by a p<0.05 and a fold change >2.0.

In serum, MMP2 and MMP3 were highest in the normal dogs and lowest in the Pre-Op OA dogs. MMP2 was significantly higher in normal dogs and Post-Op OA dogs compared to Pre-Op OA dogs (p=0.003; p=0.03), but there was not a significant difference between normal and Post-Op OA dogs. MMP3 was significantly higher in normal dogs and Post-Op OA dogs compared to Pre-Op OA dogs (p=0.002; p=0.03), but there was not a significant difference between Pre-Op and Post-Op OA dogs. Significant differences were not detected between groups for IL8, KC, MCP1, IL18, IL2, IL7 or GMCSF, and the remaining analytes were below the limit of detection for the assay.

Thus, ROC curve analysis demonstrates for the first time that a biomarker panel measuring synovial fluid MCP1, IL8, KC, MMP2 and MMP3 has the ability to consistently differentiate normal healthy knees from knees in dogs with spontaneously occurring clinical OA. In addition, MCP1 was significantly lower in the Post-Op OA dogs compared to their Pre-Op OA values, and IL8 and KC declined after treatment as well, indicating that this novel biomarker panel has great potential for clinical use in both diagnostic and treatment monitoring applications. The three cytokines were able to repeatedly distinguish between Pre-Op OA and Post-Op OA individuals (AUC=0.9) when they were measured in the synovial fluid, but the addition of MMP2 and MMP3 to the panel improved the performance (AUC=1.0), indicating that the addition of MMPs to this or any diagnostic biomarker panel would be useful for treatment monitoring or prognosis. Thus the results show that use of synovial fluid biomarkers has important clinical application based on the relative ease in obtaining samples, the associated costs, and the joint specific nature of these evaluations. Addition of MMPs to the biomarker panel enhances its capabilities, especially with respect to treatment monitoring.

Example 3

OA Biomarkers in Synovial Fluid of Human Patients

OA biomarkers in the synovial fluid of human patients were investigated. Specific goals were 1) to identify and measure the concentration of specific MMPs and inflammatory cytokines released to the synovial fluid of normal and OA patients undergoing total knee arthroplasty; and 2) to correlate the production of these inflammatory biomarkers with radiographic severity of disease. All procedures were performed with IRB (IRB#1042248) approval. Synovial fluid was aspirated from three "true normal" patients (23, 27, 28 y/o) with no previous knee injury, clinical symptoms of knee pain or OA, or operative procedures performed. Synovial fluid was aspirated from 18 patients (21 knees) with OA immediately preceding their total knee arthroplasty procedure (age range=44-86 y/o). Equal volumes of hyaluronidase treated synovial fluid samples were analyzed using the Fluorokine MAP human MMP (MMP-1, -2, -9, and 013) and cytokine (Interleukin 1f3 (IL-1f3), IL-6, IL-8, Tumor necrosis factor-α (TNF-α), Macrophage inflammatory protein 1α (MIP-1α), MIP-1f3, Monocyte chemotactic protein 1 (MCP-1), RANTES) multiplex panels (R&D Systems). A log transformation was performed to normalize the data for statistical analysis. Results from the normal and OA groups were evaluated using an unpaired t-test and between analytes using a Pearson product moment correlation. Significance was set at p<0.05. Each patient eventually undergoing TKA had a standing AP radiograph performed during the pre-operative evaluation. The Modified Kellgren and Lawrence scoring system was applied to both the medial and lateral compartments and then totaled. The radiographic scores were correlated with the log transformed MMP/cytokine data using Spearman rank order correlation with significance set at p<0.05.

Figure 3:
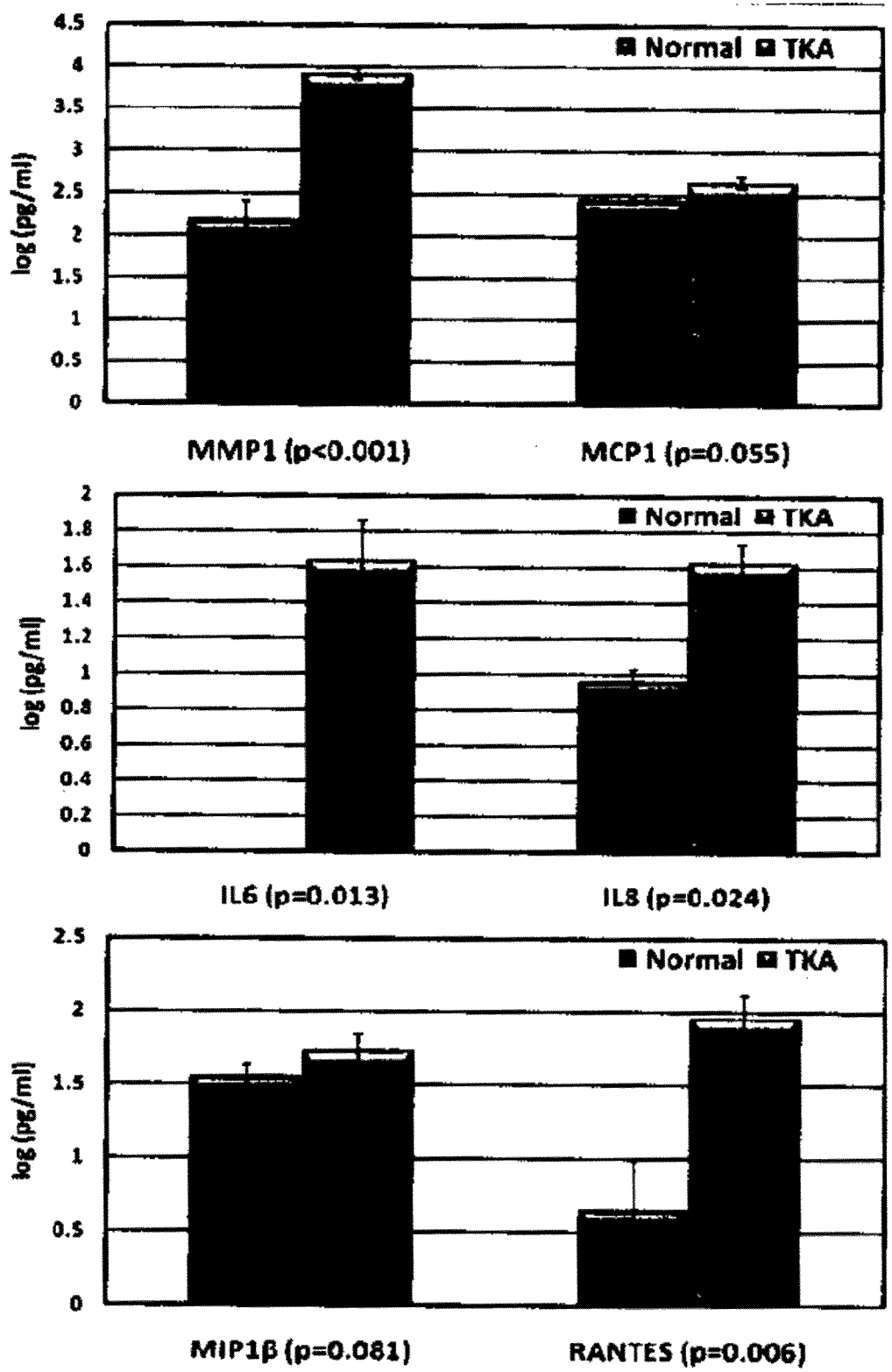
FIG. 3 is a set of bar graphs summarizing (Mean±SE) MMP/cytokine log (pg/ml) levels in synovial fluid samples from normal patients and from patients with OA immediately preceding a total knee arthroplasty procedure.

Normal vs. OA: Of the 12 biomarkers tested, MMP-1, IL-6, IL-8, and RANTES were significantly higher in the synovial fluid of OA patients compared to normal patients, as shown in FIG. 3. Three of the twelve were trending toward significance: MIP-1f3, MCP-1, and MMP-2 (not represented in FIG. 3, p=0.105). MMP-9, MMP-13, IL-lf3, TNF-α, and MIP-1α were below the detection limits of this assay for all patients.

Correlation between Analytes: MMP-1 had a moderate positive correlation with MMP-2 (r=0.43), IL-6 (r=0.52), IL-8 (r=0.43), and RANTES (0.58). IL-6 had a strong (r=0.79) positive correlation with IL-8 and a moderate (r=0.44) positive correlation with MMP-2. MCP-1 had a moderate (r=0.56) positive correlation with IL-6 and strong (r=0.70) positive correlation with IL-8.

Correlation with Radiographic Scoring: The radiographic scoring system had strong positive correlations with IL-6 (r=0.71) and IL-8 (r=0.82), and moderate positive correlations with MMP-1 (r=0.353) and MCP-1 (r=0.483).

It is believed this data provides for the first time an indication of synovial fluid biomarkers for OA in human patients. Importantly, true normal controls were used for this study, which is not often the case and thus a major limiting factor in human clinical studies. The results from this study suggest that IL-6 and IL-8 are particularly intriguing as potential biomarkers as a significant increase in these two cytokines was shown in OA patients, and also a strong correlation between the two, and strong correlations to severity of radiographic change. Also shown was a moderately strong correlation noted between severity of radiographic change and MMP-1 and MCP-1 levels. The correlations to radiographic severity are particularly important as it provides an immediate clinical relevance to the investigation of these proteins as OA biomarkers. IL-6, IL-8, MMP-1, and MCP-1 can readily be assessed as a panel in small volume samples of synovial fluid using a commercially available assay.

The results from this Example together with the results of Examples 1 and 2 show that IL-6, IL-8, MMPs, KC, and MCP-1 provide a biomarker panel for both presence and severity of disease and treatment monitoring in both canine and human patients.

Example 4

Validation of Novel OA Biomarker Panels for Distinguishing and Determining the Severity of Various Forms of Arthritis in Dogs Further study can be used to validate the novel OA biomarker panels for distinguishing and determining the severity of various forms of arthritis in dogs. A starting hypothesis is that the novel OA biomarker panel can have high sensitivity and specificity (>0.9) and ROC data (>0.8) for determining the presence and severity of OA in clinical cohorts of canine patients. To validate a novel OA biomarker panel for diagnosis and disease staging in clinical canine patients, synovial fluid, urine, and blood is collected via routine arthrocentesis, cystocentesis, and jugular venipuncture, respectively, from dogs (n=20 per group minimum) with normal stifles (knees), stifles affected by infectious arthritis, stifles affected by a developmental disorder (patellar luxation), and stifles affected by a degenerative disorder (cruciate ligament disease) upon presentation to our Veterinary Medical Teaching Hospital (VMTH). The University of Missouri's VMTH admits well over 100 cases in each of these cohorts each year. Epidemiologic data is obtained and recorded in the medical record for each case.

Clinical Assessments—Clinical lameness scores are determined and scores assigned in blinded fashion by two veterinary orthopedic surgeons based on visual examination of gait using an established scoring system (10). Comfortable range of motion (CROM) in each stifle is determined by placing a goniometer on each limb such that one arm of the goniometer is aligned with the femur and one arm is aligned with the tibia with the rotation point centered at the joint line. Each stifle is flexed and extended to the point allowable without definitive resistance or signs of pain from the dog. The maximal flexion and extension angles is recorded. This procedure is repeated 3 times. The CROM is determined by subtracting the mean flexion angle from the mean extension angle for each stifle.

Radiographic Assessment—The dogs are sedated to obtain craniocaudal and mediolateral digital radiographic views of affected stifles. The radiographs are scored by one investigator blinded to information regarding patient cohort and clinical signs, utilizing a subjective scoring system. (13, 31). For this scoring methodology, nine regions of the stifle are evaluated and given a score from 0-3 based on severity of secondary radiographic changes associated with clinical OA in dogs. Therefore, each stifle receives a score ranging from 0-27. Stifles scored from 0 to 4 are considered normal. Stifles scored from 5 to 9 are considered to have mild OA. Stifles scored from 10-18 are considered to have moderate OA, and stifles scored 19-27 are considered to have severe OA.

Arthroscopic Assessment—Arthroscopic evaluation of affected stifles are performed using craniolateral and craniomedial portals. All articular surfaces of the patella, femur and tibia are examined and scored with respect to degree of articular cartilage damage (ICRS system). Meniscal, ligamentous, and synovial pathology are arthroscopically assessed and described in terms of nature, extent, and location. Dogs in the normal stifle group do not undergo arthroscopy.

Biomarkers—A small aliquot (25 μl) from each sample is thawed. For urine and synovial fluid, samples are centrifuged at 14,000 rpm for 10 minutes to pellet debris, and the supernatant removed. Synovial fluid samples are incubated with hyaluronidase (MP Biomedicals, LLC, Solon, Ohio) at 37° C. for 60 minutes to decrease viscosity. Each aliquot of synovial fluid, urine, and serum is analyzed in duplicate using multiplex immunoassays based on the xMAP platform (Qiagen Inc., Valencia, Calif.) for IL-lf3, IL-2, IL-4, IL-6, IL-7, IL-8, IL-10, IL-15, IL-18, IP-10, 15 INF-γ, TNF-α, MCP1, KC, GM-CSF, COMP, Apo1, Apo2, MIP-1α), MIP-1f3 MMP1, MMP2, MMP3, MMP9 and MMP13 according to the manufacturers' directions. Briefly, each of the samples is admixed with monoclonal antibody-charged, small (5.6 micron), polystyrene microspheres in a 96-well plate. Following an overnight incubation at 4° C., a polyclonal secondary antibody is added, as well as streptavidin-phycoerythrin. The median fluorescence intensity (MFI) is determined for each sample, and concentrations (pg/ml) obtained from a standard curve.

Statistical Analyses—Strength of correlations between each biomarker and combinations of biomarkers to detect presence and stage of disease is analyzed using a Pearson's Correlation. Sensitivity, specificity, and receiver operating characteristic curve (ROC) data is calculated for each biomarker and combinations of biomarkers to determine discriminatory potential between presence, type, and severity of disease for the various cohorts based on all outcome measures employed.

Example 5

Validation of Novel OA Biomarker Panels for Distinguishing and Determining the Severity of Various Forms of Arthritis in Humans Further study can also be used to validate the novel OA biomarker panels for diagnosis and disease staging in clinical human patients. With informed patient consent under IRB approval, synovial fluid, urine, and blood is collected via routine arthrocentesis, free catch urine collection, and peripheral venipuncture, respectively, from patients (n=20 per group minimum) with normal knees, knees with rheumatoid arthritis, knees with meniscal tears and grade 1-2 articular cartilage pathology, knees with post-traumatic OA, and knees with end stage OA undergoing total knee arthroplasty at The University of Missouri Hospitals and Clinics (UMHC).

The UMHC admits well over 200 cases in each of these cohorts each year. Epidemiologic data is obtained and recorded in the medical record for each case.

Clinical Assessments—Knee examination is performed on all participants and findings recorded. The 36-Item Short-Form Health Survey (SF-36) is used to assess the patient quality of life. 2 This is a self-reported multidomain questionnaire, reflecting the patient's pain, strength, and affect secondary to their disease. Functional outcome measures is assessed via the Western Ontario McMaster Universities Osteoarthritis Index (WOMAC)(34).

Radiographic Assessment—Knee radiographs are assessed using the Modified Kellgren-Lawrence scoring system (21) where the medial and lateral compartments is reviewed, scored for the severity of changes and then scores totaled.

Whole-joint Surgical Assessment—At the time of surgery (arthrotomy or arthroscopy), all articular surfaces of the patella, femur and tibia are examined and scored with respect to degree of articular cartilage damage (ICRS system). Meniscal, ligamentous, and synovial pathology are assessed and described in terms of nature, extent, and location. Patients in the normal group do not undergo surgical assessment.

Biomarkers—A small aliquot (25 µl) from each sample is thawed. For urine and synovial fluid, samples are centrifuged at 14,000 rpm for 10 minutes to pellet debris, and the supernatant removed. Synovial fluid samples are incubated with hyaluronidase (MP Biomedicals, LLC, Solon, Ohio) at 37° C. for 60 minutes to decrease viscosity. Each aliquot of synovial fluid, urine, and serum is analyzed in duplicate using multiplex immunoassays based on the xMAP platform (Qiagen Inc., Valencia, Calif.) for IL-1f3, IL-2, IL-4, IL-6, IL-7, IL-8, IL-10, IL-15, IL-18, IP-10, INF-γ, TNF-α, MCP1, KC, GM-CSF, COMP, Apo1, Apo2, MIP-1a), MIP-1f3 MMP1, MMP2, MMP3, MMP9 and MMP13 according to the manufacturers' directions. Briefly, each of the samples is admixed with monoclonal antibody-charged, small (5.6 micron), polystyrene microspheres in a 96-well plate. Following an overnight incubation at 4° C., a polyclonal secondary antibody is added, as well as streptavidin-phycoerythrin. The median fluorescence intensity (MFI) is determined for each sample, and concentrations (pg/ml) obtained from a standard curve.

Statistical Analyses—Strength of correlations between each biomarker and combinations of biomarkers to detect presence and stage of disease is analyzed using a Pearson's Correlation. Sensitivity, specificity, and receiver operating characteristic curve (ROC) data is calculated for each biomarker and combinations of biomarkers to determine discriminatory potential between presence, type, and severity of disease for the various cohorts based on all outcome measures employed.

The present disclosure illustratively described herein suitably may be practiced in the absence of any element or elements, limitation or limitations which are not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

REFERENCES

1. Andersson M L E, Thorstensson C A, Roos E M, Petersson I F, Heinegård D, Saxne T. Serum levels of Cartilage Oligomeric Matrix Protein (COMP) increase temporarily after physical exercise in patients with knee osteoarthritis. BMC Musculoskeletal Disorders. 2006; 7.
2. Angst F, Aeschlimann A, Steiner W, Stucki G. Responsiveness of the WOMAC osteoarthritis index as compared with the SF-36 in patients with osteoarthritis of the legs undergoing a comprehensive rehabilitation intervention. Annals of the Rheumatic Diseases. 2001; 60(9):834-840.
3. Bay-Jensen A C, Andersen T L, Charni-Ben Tabassi N, Kristensen P W, Kjaersgaard-Andersen P, Sandell L, Garnero P, Delaissé J M. Biochemical markers of type II collagen breakdown and synthesis are positioned at specific sites in human osteoarthritic knee cartilage. Osteoarthritis and Cartilage. 2008; 16(5):615-623.
4. Blackburn Jr W D, Chivers S, Bernreuter W. Cartilage imaging in osteoarthritis. Seminars in Arthritis and Rheumatism. 1996; 25(4):273-281.
5. Chan W P, Lang P, Stevens M P, Sack K, Majumdar S, Stoller D W, Basch C, Genant H K. Osteoarthritis of the knee: Comparison of radiography, CT, and MR imaging to assess extent and severity. American Journal of Roentgenology. 1991; 157(4):799-806.
6. Chua Jr S D, Messier S P, Legault C, Lenz M E, Thonar EJMA, Loeser R F. Effect of an exercise and dietary intervention on serum biomarkers in overweight and obese adults with osteoarthritis of the knee. Osteoarthritis and Cartilage. 2008; 16(9):1047-1053.

7. Cook J L, Fox D B, Malaviya P, Tomlinson J L, Farr J, Kuroki K, Cook C R. Evaluation of small intestinal submucosa grafts for meniscal regeneration in a clinically relevant posterior meniscectomy model in dogs. The journal of knee surgery. 2006; 19(3):159-167.
8. Cook J L, Kuroki K, Kenter K, Marberry K, Brawner T, Geiger T, Jayabalan P, Bal B S. Bipolar and monopolar radiofrequency treatment of osteoarthritic knee articular cartilage: acute and temporal effects on cartilage compressive stiffness, permeability, cell synthesis, and extracellular matrix composition. The journal of knee surgery. 2004; 17(2):99-108.
9. Cook J L, Tomlinson J L, Arnoczky S P, Fox D B, Reeves Cook C, Kreeger J M. Kinetic study of the replacement of porcine small intestinal submucosa grafts and the regeneration of meniscal-like tissue in large avascular meniscal defects in dogs. Tissue Engineering. 2001; 7(3):321-334.
10. Cook J L, Tomlinson J L, Kreeger J M, Cook C R. Induction of meniscal regeneration in dogs using a novel biomaterial. American Journal of Sports Medicine. 1999; 27(5):658-665.
11. Cook J L, Williams N, Kreeger J M, Peacock J T, Tomlinson J L. Biocompatibility of three-dimensional chondrocyte grafts in large tibial defects of rabbits. American Journal of Veterinary Research. 2003; 64(1): 12-20.
12. Dvorak L D, Cook J L, Kreeger J M, Kuroki K, Tomlinson J L. Effects of carprofen and dexamethasone on canine chondrocytes in a three-dimensional culture model of osteoarthritis. American Journal of Veterinary Research. 2002; 63(10):1363-1369.
13. Fettig A A, Rand W M, Sato A F, Solano M, McCarthy R J, Boudrieau R J. Observer Variability of Tibial Plateau Slope Measurement in 40 Dogs with Cranial Cruciate Ligament—Deficient Stifle Joints. Veterinary Surgery. 2003; 32(5):471-478.
14. Fox D B, Cook J L. Synovial fluid markers of osteoarthritis in dogs. Journal of the American Veterinary Medical Association. 2001; 219(6):756-761.
15. Garcia-Seco E, Wilson D A, Cook J L, Kuroki K, Kreeger J M, Keegan K G. Measurement of articular cartilage stiffness of the femoropatellar, tarsocrural, and metatarsophalangeal joints in horses and comparison with biochemical data. Veterinary Surgery. 2005; 34(6):571-578.
16. Garner B C S A, Cook J L. Change in cytokine and chemokine levels in the synovial fluid, serum and urine of dogs with surgically induced osteoarthritis. 56th Annual Orthopaedic Research Society Meeting. 2010.
17. Garnero P, Aronstein W S, Cohen S B, Conaghan P G, Cline G A, Christiansen C, Beary J F, Meyer J M, Bingham Iii C O. Relationships between biochemical markers of bone and cartilage degradation with radiological progression in patients with knee osteoarthritis receiving risedronate: the Knee Osteoarthritis Structural Arthritis randomized clinical trial. Osteoarthritis and Cartilage. 2008; 16(6):660-666.
18. Greenberg D D, Stoker A, Kane S, Cockrell M, Cook J L. Biochemical effects of two different hyaluronic acid products in a co-culture model of osteoarthritis. Osteoarthritis and Cartilage. 2006; 14(8):814-822.
19. Henrotin Y, Addison S, Kraus V, Deberg M. Type II collagen markers in osteoarthritis: What do they indicate? Current Opinion in Rheumatology 2007; 19(5):444-450.
20. Hou Y, Wang Y, Lust G, Zhu L, Zhang Z, Todhunter R J. Retrospective analysis for genetic improvement of hip joints of cohort labrador retrievers in the U.S. Ser. No. 19/702,007. PLoS ONE. 5(2).
21. Kellgren J H, Lawrence J S. Radiological assessment of osteo-arthrosis. Annals of the Rheumatic Diseases. 1957; 16(4):494-502.
22. Kuroki K, Cook J L, Kreeger J M. Mechanisms of action and potential uses of hyaluronan in dogs with osteoarthritis. Journal of the American Veterinary Medical Association. 2002; 221(7):944-950.
23. Kuroki K, Cook J L, Kreeger J M, Tomlinson J L. The effects of TIMP-1 and -2 on canine chondrocytes cultured in three-dimensional agarose culture system. Osteoarthritis and Cartilage. 2003; 11(9):625-635.
24. Kuroki K, Cook J L, Stoker A M, Turnquist S E, Kreeger J M, Tomlinson J L. Characterizing osteochondrosis in the dog: Potential roles for matrix metalloproteinases and mechanical load in pathogenesis and disease progression. Osteoarthritis and Cartilage. 40 2005; 13(3):225-234.
25. Lawrence R C, Felson D T, Helmick C G, Arnold L M, Choi H, Deyo R A, Gabriel S, Hirsch R, Hochberg M C, Hunder G G, Jordan J M, Katz J N, Kremers H M, Wolfe F. Estimates of the prevalence of arthritis and other rheumatic conditions in the United States. Part II. Arthritis and Rheumatism. 2008; 58(1):26-35.
26. Mazières B, Garnero P, Guéguen A, Abbal M, Berdah L, Lequesne M, Nguyen M, Salles J P, Vignon E, Dougados M. Molecular markers of cartilage breakdown and synovitis at baseline as predictors of structural progression of hip osteoarthritis. The ECHODIAH* cohort. Annals of the Rheumatic Diseases. 2006; 65(3):354-359.
27. Mazzuca S A, Brandt K D, Eyre D R, Katz B P, Askew J, Lane K A. Urinary levels of type II collagen C-telopeptide crosslink are unrelated to joint space narrowing in patients with knee osteoarthritis. Annals of the Rheumatic Diseases. 2006; 65(8):1055-1059.
28. Nganvongpanit K, Pothacharoen P, Chaochird P, Klunklin K, Warrit K, Settakorn J, Pattamapaspong N, Luevitoonvechkij S, Arpornchayanon O, Kongtawelert P, Pruksakorn D. Prospective evaluation of serum biomarker levels and cartilage repair by autologous chondrocyte transplantation and subchondral drilling in a canine model. Arthritis Research and Therapy. 2009; 11(3).
29. Poole A R. Biochemical/immunochemical biomarkers of osteoarthritis: Utility for prediction of incident or progressive osteoarthritis. Rheumatic Disease Clinics of North America. 2003; 29(4):803-818.
30. Ray A, Kuroki K, Cook J L, Bal B S, Kenter K, Aust G, Ray BK. Induction of matrix metalloproteinase 1 gene expression is regulated by inflammation-responsive transcription factor SAF-1 in osteoarthritis. Arthritis and Rheumatism. 2003; 48(1):134-145.
31. Roy R G, Wallace L J, Johnston G R, Wickstrom S L. A retrospective evaluation of stifle osteoarthritis in dogs with bilateral medial patellar luxation and unilateral surgical repair.
32. Veterinary surgery: VS: the official J. of the Am. Coll. of Vet. Surg., 1992; 21(6):475-479.
33. Stoker A M, Cook J L, Kuroki K, Fox D B. Site-specific analysis of gene expression in early osteoarthritis using the Pond-Nuki model in dogs. Journal of Orthopaedic Surgery and Research. 2006; 1(1).
34. van Spil W E, DeGroot J, Lems W F, Oostveen J C M, Lafeber FPJG. Serum and urinary biochemical markers for knee and hip-osteoarthritis: A systematic review applying the consensus BIPED criteria. Osteoarthritis and Cartilage. 2010; 18(5):605-612.

35. Ware Jr J E, Sherbourne C D. The MOS 36-item short-form health survey (SF-36). I. Conceptual framework and item selection. Medical Care. 1992; 30(6):473-483.
36. Wilke V L, Robinson D A, Evans R B, Rothschild M F, Conzemius M G. Estimate of the annual economic impact of treatment of cranial cruciate ligament injury in dogs in the United States. J. of the American Veterinary Medical Association. 2005; 227(10): 1604-1607.
37. Yoshimura M, Sakamoto K, Tsuruta A, Yamamoto T, Ishida K, Yamaguchi H, Nagaoka I. Evaluation of the effect of glucosamine administration on biomarkers for cartilage and bone metabolism in soccer players. International Journal of Molecular Medicine. 2009; 24(4):487-494.

What is claimed is:

1. A method to detect osteoarthritis in a human subject comprising:
   (a) using a protein detection method to determine the levels of three or more different osteoarthritis marker polypeptides in a synovial fluid sample collected from a first human subject, wherein the three or more different osteoarthritis marker polypeptides comprise MCP1, IL8, and KC;
   (b) using the protein detection method to determine the levels of three or more different osteoarthritis marker polypeptides in a biological fluid sample collected from a second human control subject, wherein the three or more different osteoarthritis marker polypeptides comprise MCP1, IL8, and KC;
   (c) using the level of each of the three or more different osteoarthritis marker polypeptides in the first human subject and the second human control subject to calculate a probability of the presence of osteoarthritis in the first human subject, and determining whether the probability is greater than or equal to at least about 80%; and
   (d) when the probability from step (c) is greater than or equal to at least about 80%, determining that osteoarthritis is present in the first human subject.

2. The method of claim 1, wherein the level of expression of at least one additional osteoarthritis marker polypeptide is measured.

3. The method of claim 2, wherein the at least one additional osteoarthritis marker polypeptide is selected from the group consisting of MMP2 and MMP3.

4. The method of claim 2, comprising measuring in the biological fluid samples from the human test and control subjects the level of expression of MCP1, IL8, KC, MMP2 and MMP3.

5. The method of claim 4, further comprising measuring in the biological fluid samples from the human test and control subjects the level of expression of at least one additional osteoarthritis marker selected from Apolipoprotein A1 and Apolipoprotein E.

6. The method of claim 5, wherein the level of expression of at least seven different osteoarthritis marker polypeptides is measured, wherein the selected osteoarthritis marker polypeptides comprise MCP-1, IL8, KC, MMP2, MMP3, Apolipoprotein A1 and Apolipoprotein E.

7. The method of claim 1, wherein the first human subject is at risk of having osteoarthritis.

8. The method according to claim 1, wherein the protein detection method is selected from the group consisting of: LUMINEX, ELISA, immunoassay, mass spectrometry, high performance liquid chromatography, two-dimensional electrophoresis, Western blotting, protein microarray, and antibody microarray.

9. The method of claim 8, wherein the protein detection method is an immunoassay.

10. The method of claim 1, wherein the probability is calculated in a method comprising the steps of: determining the levels of three or more biomarkers in the first subject and the second subject, generating a receiver operating characteristic (ROC) curve, and calculating the area under the ROC curve (AUC), the area under the curve (AUC) providing the probability of the presence of osteoarthritis in the first subject.

11. The method of claim 1, wherein the second human control subject is a true normal control subject.

12. A method to detect osteoarthritis in a human subject comprising:
   (a) using a protein detection method to determine the levels of three or more different osteoarthritis marker polypeptides in a synovial fluid sample collected from a first human subject, wherein the three or more different osteoarthritis marker polypeptides comprise MCP1, IL8, and KC;
   (b) using the protein detection method to determine the levels of three or more different osteoarthritis marker polypeptides in a biological fluid sample collected from a second human control subject, wherein the control subject is a true normal control, and wherein the three or more different osteoarthritis marker polypeptides comprise MCP1, IL8, and KC;
   (c) using the level of each of the three or more different osteoarthritis marker polypeptides in the first human subject and the second human control subject to calculate a probability of the presence of osteoarthritis in the first human subject, and determining whether the probability is greater than or equal to at least about 80%; and
   (d) when the probability from step (c) is greater than or equal to at least about 80%, determining that osteoarthritis is present in the first human subject.

* * * * *